United States Patent
Ryle et al.

(10) Patent No.: US 12,178,433 B2
(45) Date of Patent: Dec. 31, 2024

(54) BUTTRESS APPLICATOR SYSTEM FOR SURGICAL STAPLER

(71) Applicant: Cilag GmbH International, Zug (CH)

(72) Inventors: William C. Ryle, Covington, KY (US);
Evan N. Stambler, West Chester, OH (US); Kirsten N. W. Chenery, Loveland, OH (US); Daniel J. Mumaw, Liberty Township, OH (US); Tiffany M. Warner, Cincinnati, OH (US); Clinton Denlinger, Cincinnati, OH (US); Mark T. Larson, Cincinnati, OH (US); Tony C. Siebel, Cincinnati, OH (US); Pamela M. Ridgley, Lebanon, OH (US)

(73) Assignee: Cilag GmbH International, Zug (CH)

( * ) Notice: Subject to any disclaimer, the term of this patent is extended or adjusted under 35 U.S.C. 154(b) by 299 days.

(21) Appl. No.: 17/710,236

(22) Filed: Mar. 31, 2022

(65) Prior Publication Data
US 2023/0310000 A1   Oct. 5, 2023

(51) Int. Cl.
*A61B 17/072*  (2006.01)
*A61B 17/00*  (2006.01)

(52) U.S. Cl.
CPC .. *A61B 17/07292* (2013.01); *A61B 17/07207* (2013.01); *A61B 2017/00526* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .................... A61B 17/07292; A61B 17/07207
USPC ........................................................ 227/180.1
See application file for complete search history.

(56) References Cited

U.S. PATENT DOCUMENTS

| | | | |
|---|---|---|---|
| 7,380,696 | B2 | 6/2008 | Shelton, IV et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |

(Continued)

OTHER PUBLICATIONS

Chris.W Hard Eyeglasses Case Plastic Glasses Protective Case for Women Men, Magnetic Closure Small Sunglass Case—Publicly available for sale Aug. 14, 2019 on Amazon.com, URL: https://www.amazon.com/Chris-W-Transparent-Eyeglasses-Protective-Magnetic /dp/B07WJRJYP3 (Year: 2019).*

(Continued)

*Primary Examiner* — Valentin Neacsu
(74) *Attorney, Agent, or Firm* — Frost Brown Todd LLP

(57) ABSTRACT

An apparatus includes a body having an interior space sized and shaped to receive a surgical stapler end effector in an open state in combination with an adjunct applicator that includes an adjunct. The apparatus further includes a closure member movably coupled with the body. The closure member is actuatable to close the surgical stapler end effector onto the adjunct applicator so that the adjunct is applied to a stapling surface of the surgical stapler end effector.

20 Claims, 31 Drawing Sheets

(56) References Cited

U.S. PATENT DOCUMENTS

| | | |
|---|---|---|
| 10,092,292 B2 | 10/2018 | Boudreaux et al. |
| 10,166,023 B2 | 1/2019 | Vendely et al. |
| 10,349,939 B2 | 7/2019 | Shelton, IV et al. |
| 11,039,832 B2 | 6/2021 | Vendely et al. |
| 11,272,935 B2 | 3/2022 | Bakos et al. |
| 11,413,040 B2 | 8/2022 | Zeiner et al. |
| 11,419,605 B2 | 8/2022 | Denzinger et al. |
| 11,452,523 B2 | 9/2022 | Zeiner et al. |
| 11,564,683 B2 | 1/2023 | Vendely et al. |
| 11,602,347 B2 | 3/2023 | Vendely et al. |
| 11,660,093 B2 | 5/2023 | Bakos et al. |
| 11,559,306 B2 | 6/2023 | Zeiner et al. |
| 11,766,261 B2 | 9/2023 | Bakos et al. |
| 11,801,048 B2 | 10/2023 | Vendely et al. |
| 2020/0015915 A1* | 1/2020 | Swayze ............ A61B 17/07292 |
| 2022/0079583 A1* | 3/2022 | Denzinger ......... A61B 17/0686 |
| 2022/0079593 A1* | 3/2022 | Bakos .............. A61B 17/07292 |
| 2023/0310000 A1* | 10/2023 | Ryle ................ A61B 17/07292 |
| | | 227/180.1 |

OTHER PUBLICATIONS

International Search Report and Written Opinion dated Jun. 12, 2023 for Application No. PCT/IB2023/053074, 12 pgs.

\* cited by examiner

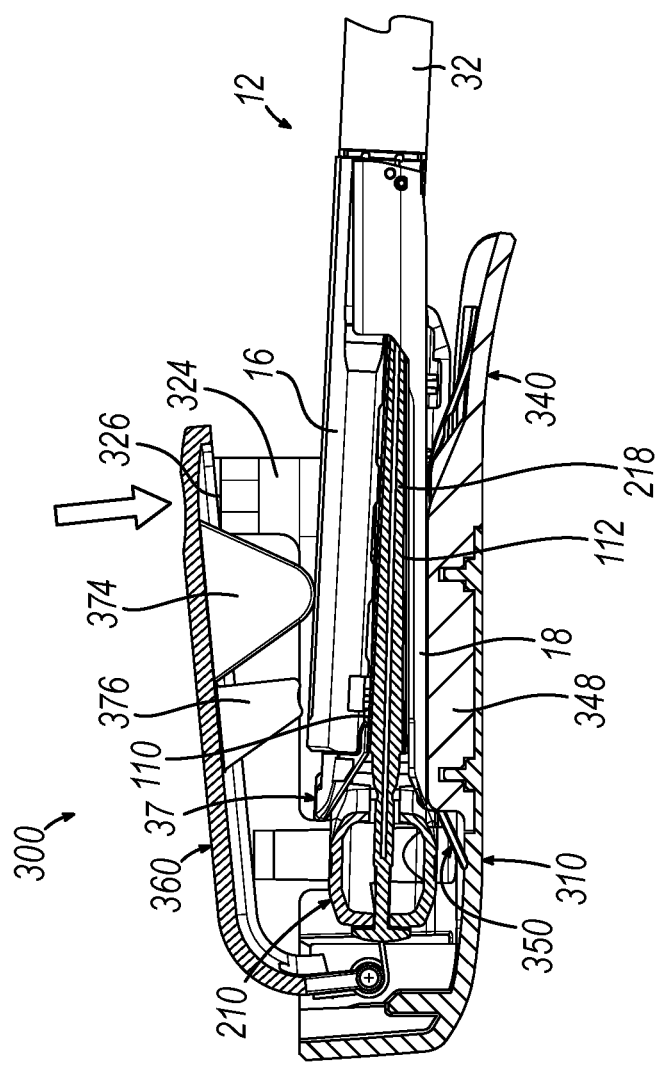

BUTTRESS APPLICATOR SYSTEM FOR SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 19C depicts a partial cross-sectional side view of the adjunct applicator system and the end effector of FIG. 19B, showing the end effector having been actuated to a closed state onto the platform of the adjunct applicator device in response to closure of the closure member of the end effector closure device so that the pair of adjuncts are applied to the stapling surfaces of the end effector jaws;

Figure 1:
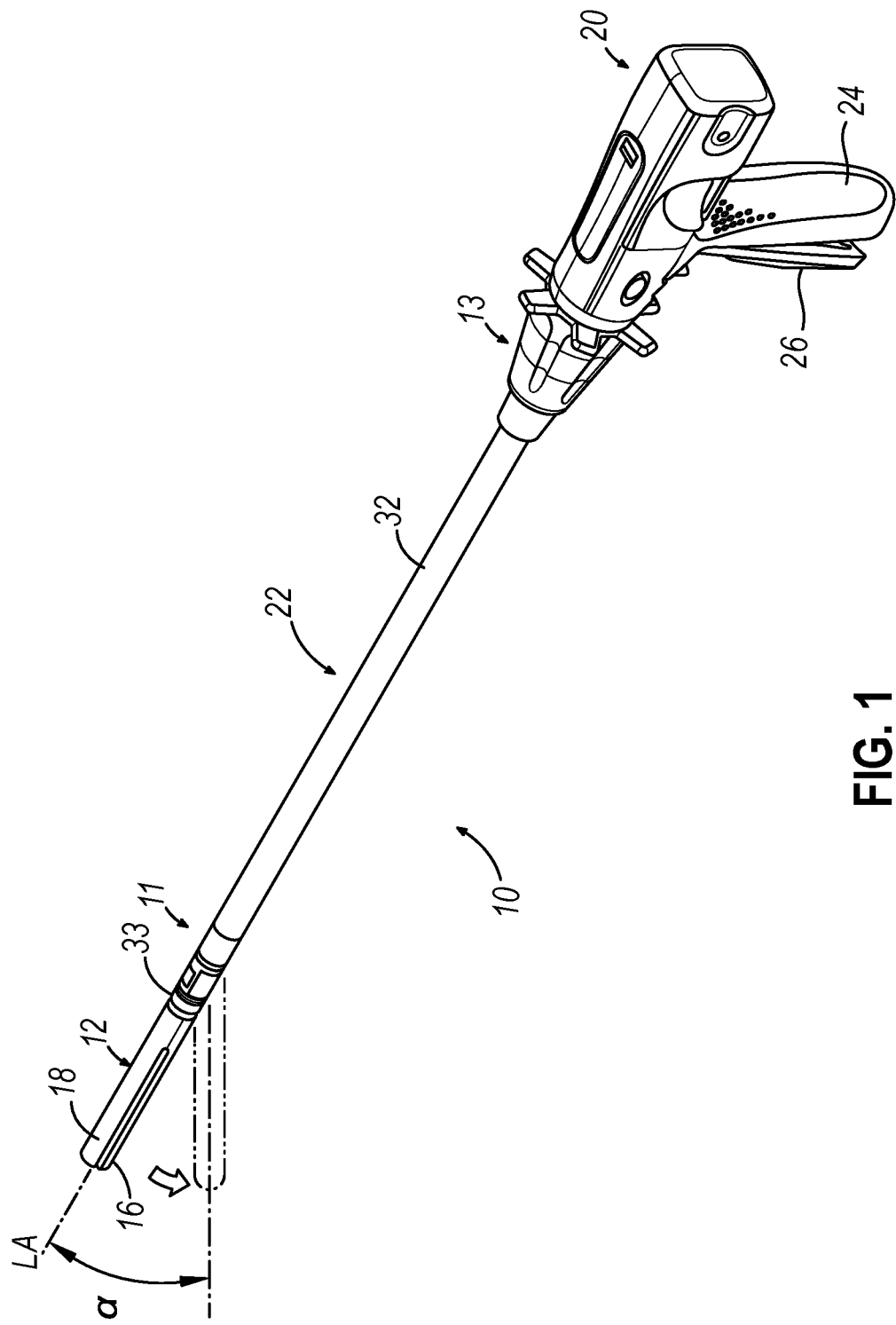
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. EXEMPLARY SURGICAL STAPLER

FIGS. 1-7 depict an exemplary surgical stapling and severing instrument (10) (also referred to herein as a surgical stapler) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
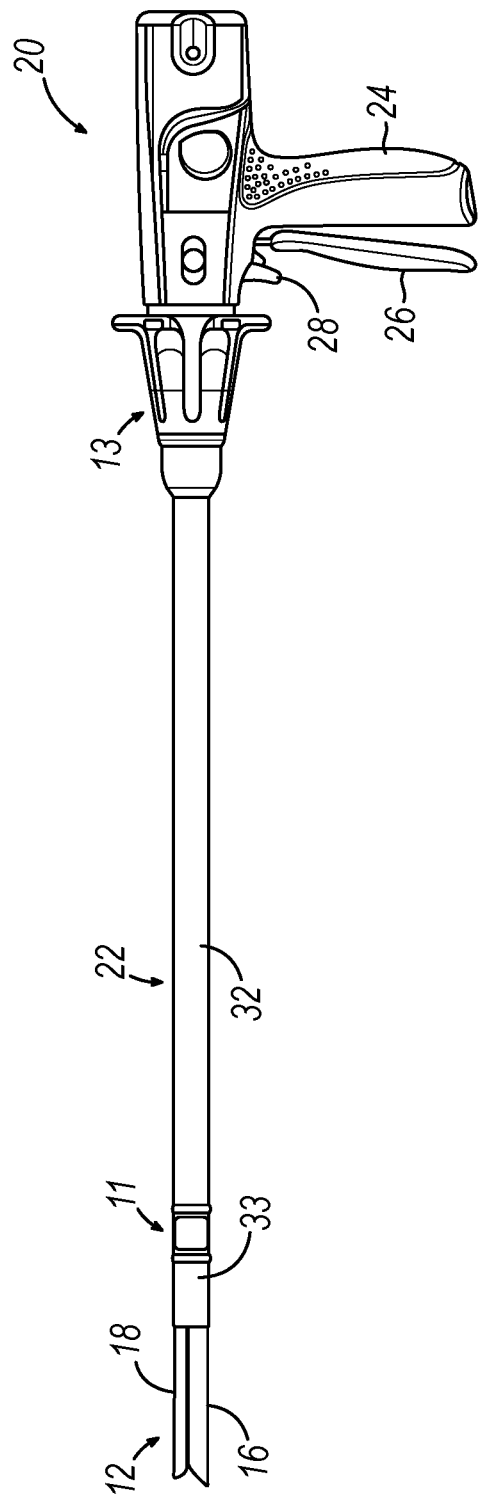
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
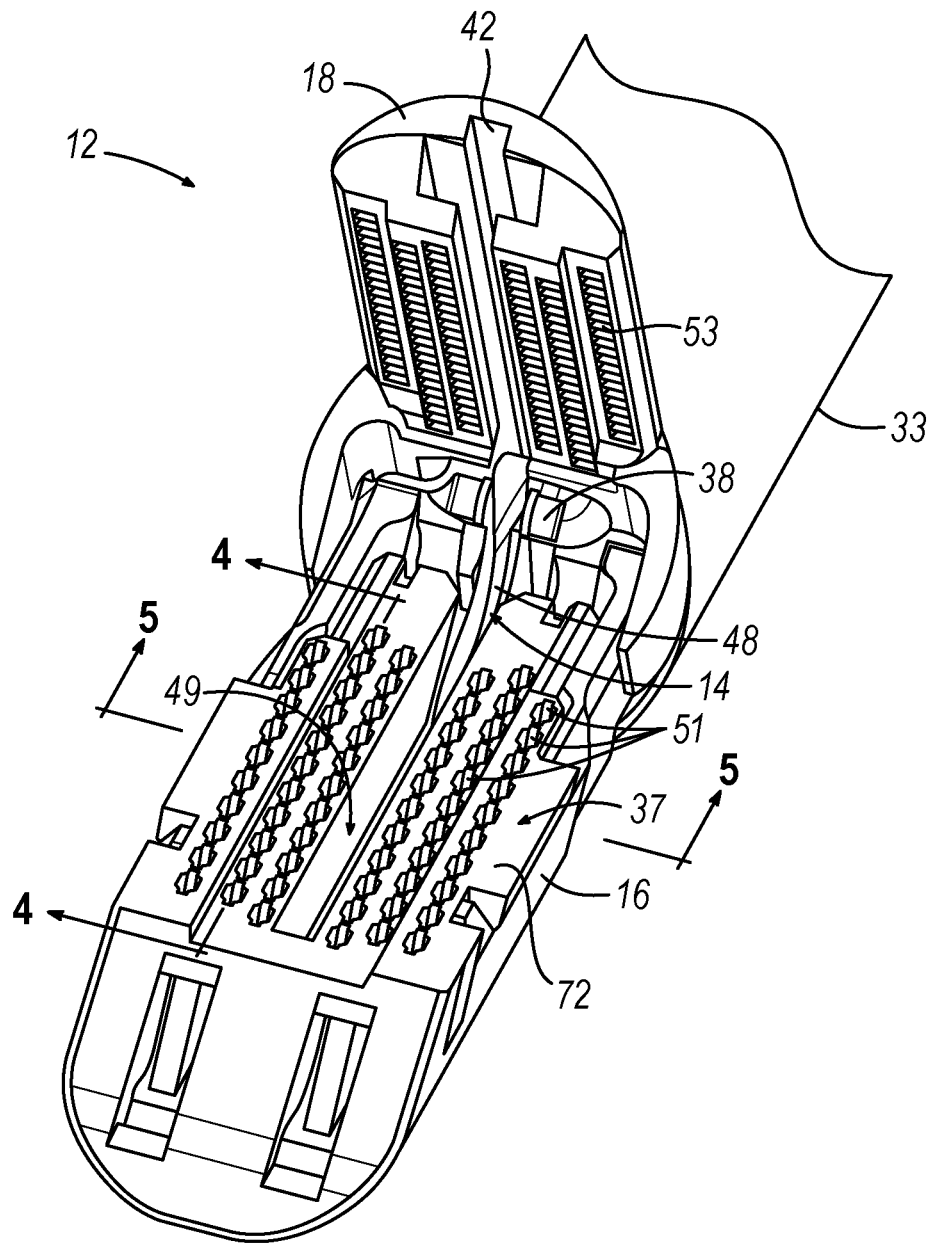
FIG. 3 depicts a perspective view of an end effector of the instrument of FIG. 1 in an open state.
Figure 4A:
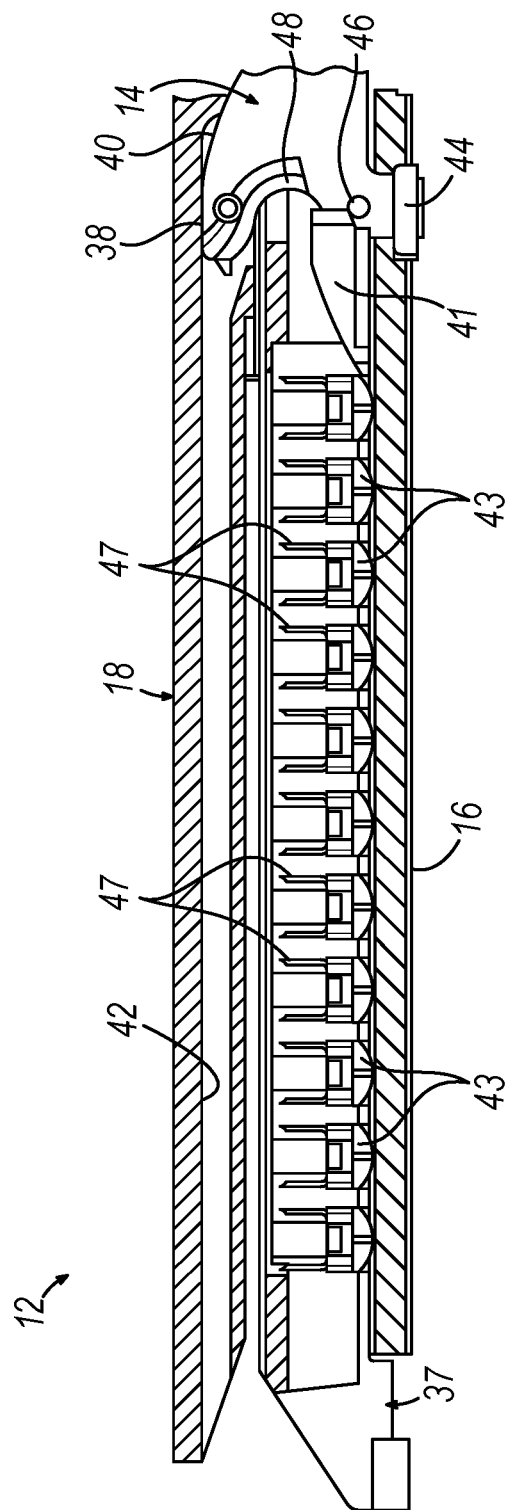
FIG. 4A depicts a side cross-sectional view of the end effector of FIG. 3, taken along line 4-4 of FIG. 3, with a firing beam in a proximal position.
Figure 4B:
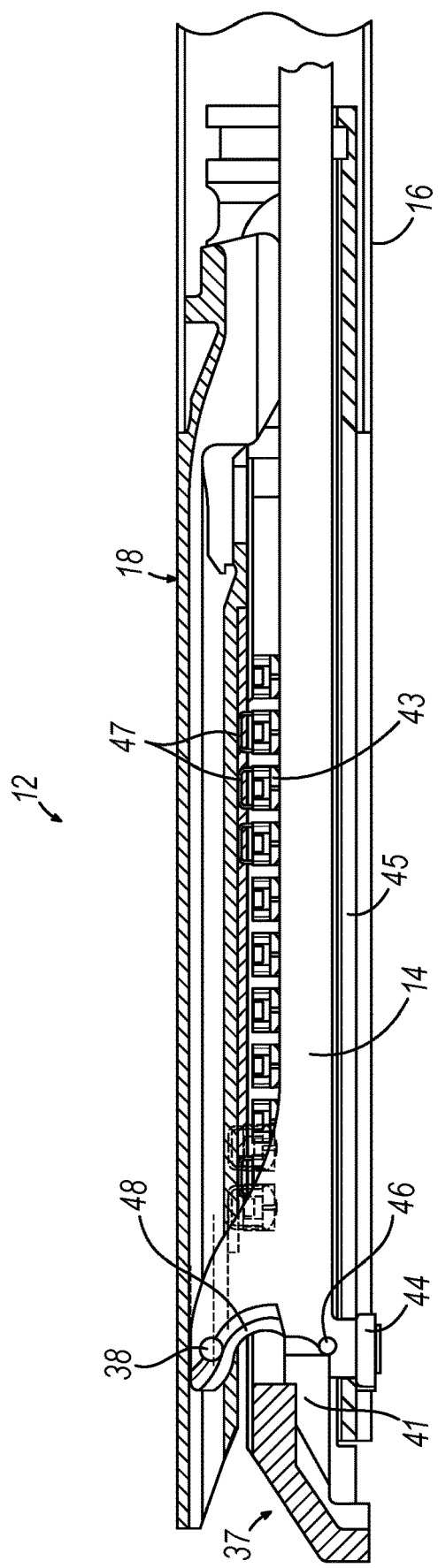
FIG. 4B depicts a side cross-sectional view of the end effector of FIG. 3, taken along line 4-4 of FIG. 3, with the firing beam in a distal position.
Figure 5:
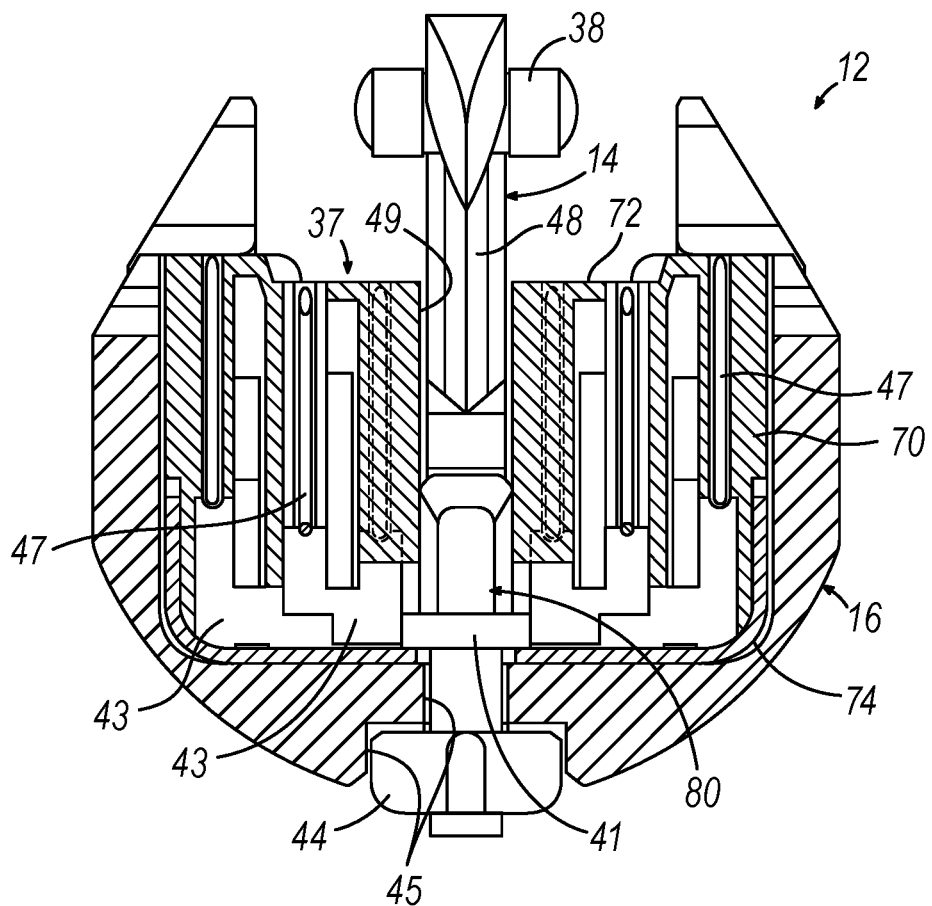
FIG. 5 depicts an end cross-sectional view of the end effector of FIG. 3, taken along line 5-5 of FIG. 3.
Figure 6:
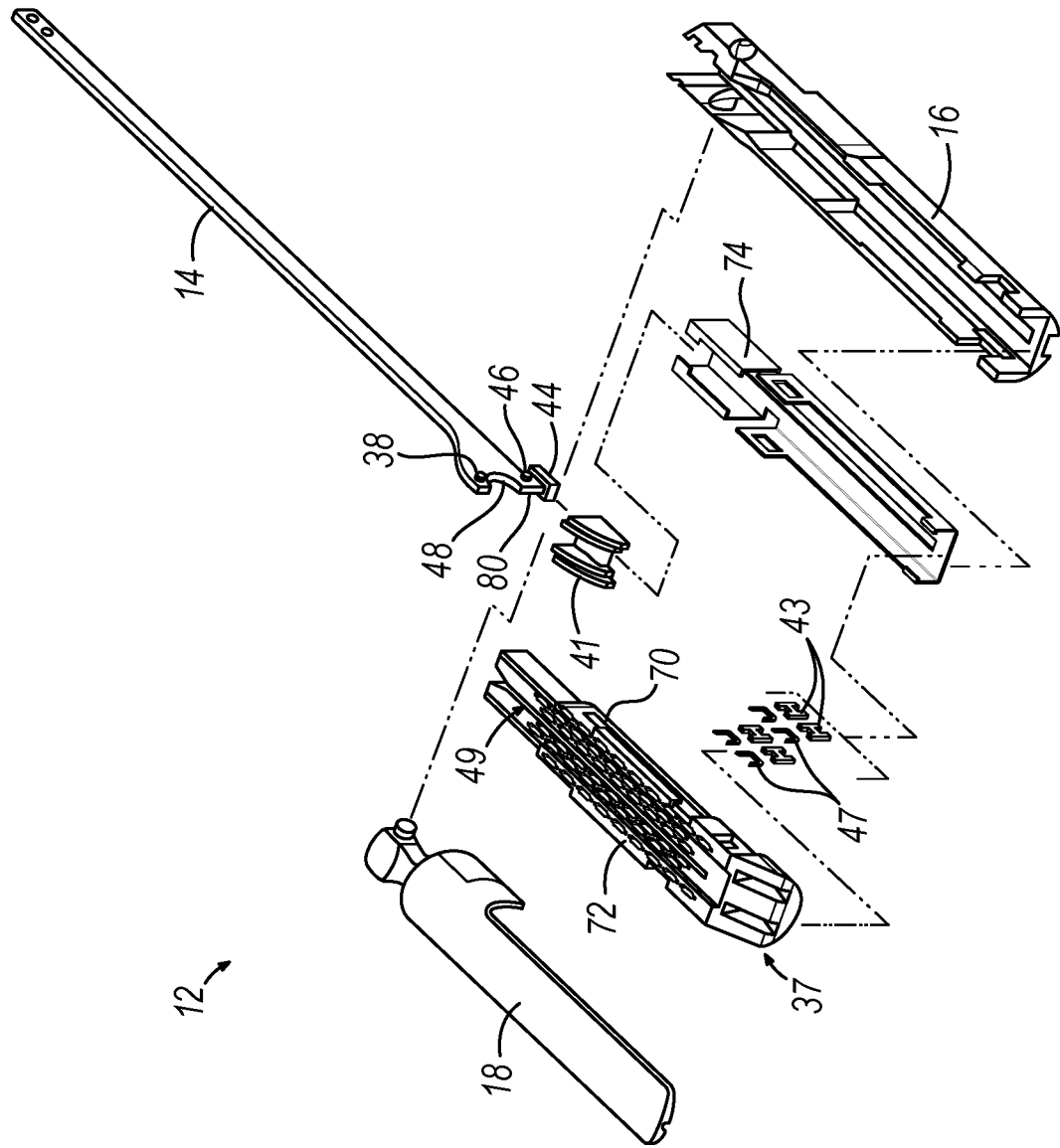
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
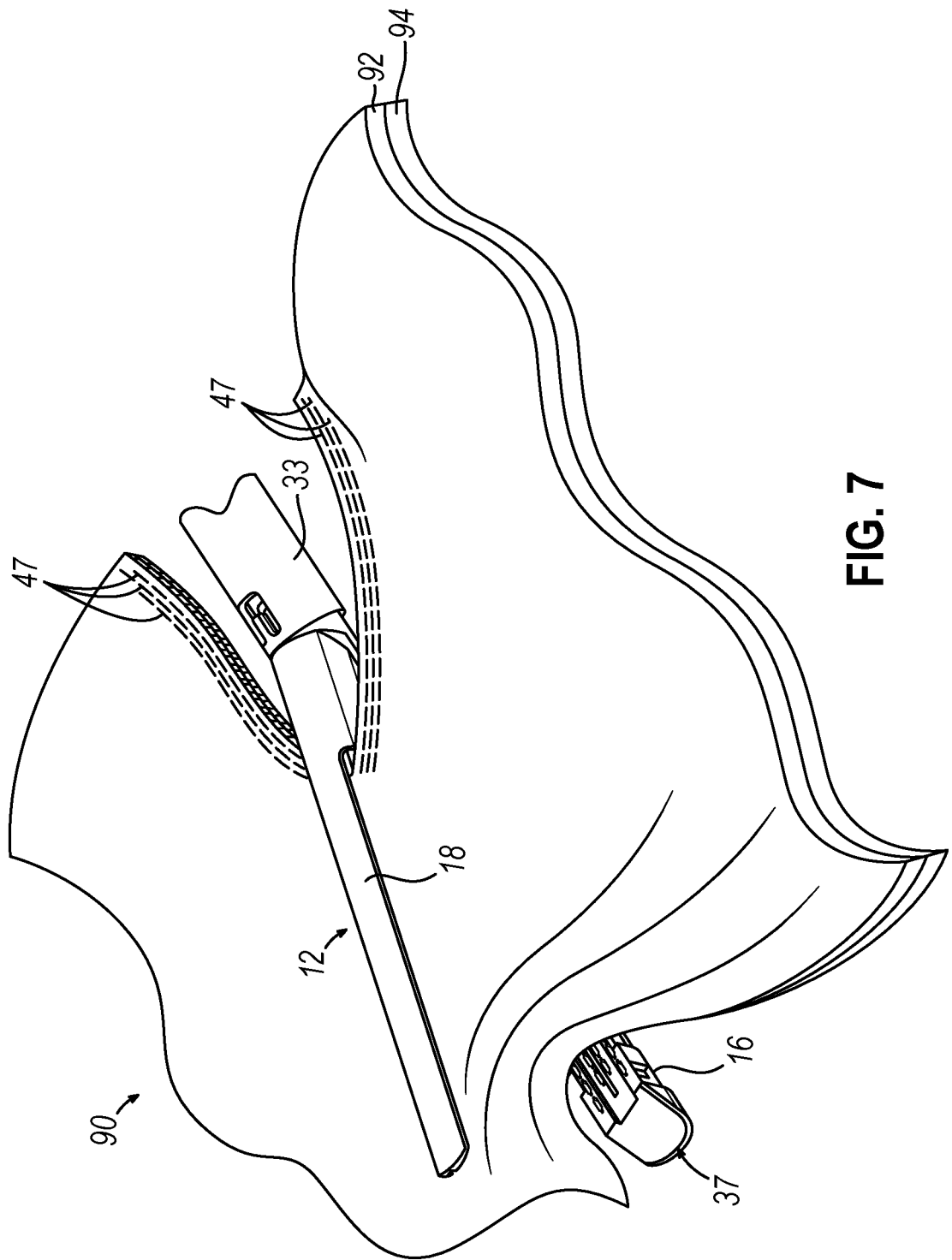
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No.

9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. EXEMPLARY BUTTRESS ASSEMBLY AND APPLICATOR DEVICE

In some instances, it may be desirable to equip the stapling surfaces defined by anvil (18) and staple cartridge (37) of end effector (12) of surgical stapler (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary applicator devices may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; U.S. Pat. No. 10,166,023, entitled "Method of Applying a Buttress to a Surgical Stapler End Effector," issued Jan. 1, 2019; U.S. Pat. No. 11,039,832, entitled "Surgical Stapler Buttress Applicator with Spent Staple Cartridge Lockout," issued Jun. 22, 2021; U.S. Pub. No. 2020/0205826, entitled "Curved Tip Surgical Stapler Buttress Assembly Applicator with Opening Feature for Curved Tip Alignment," published Jul. 2, 2020; U.S. Pub. No. 2021/0169471, entitled "Method of Applying a Buttress to a Surgical Stapler End Effector," published Jun. 10, 2021; and/or U.S. Pub. No. 2021/0346022, entitled "Method of Applying Buttresses to Surgically Cut and Stapled Sites," published Nov. 11, 2021. The disclosure of each of the above-cited patent documents is incorporated by reference herein.

A. Exemplary Composition of Buttress Assembly

Figure 8:
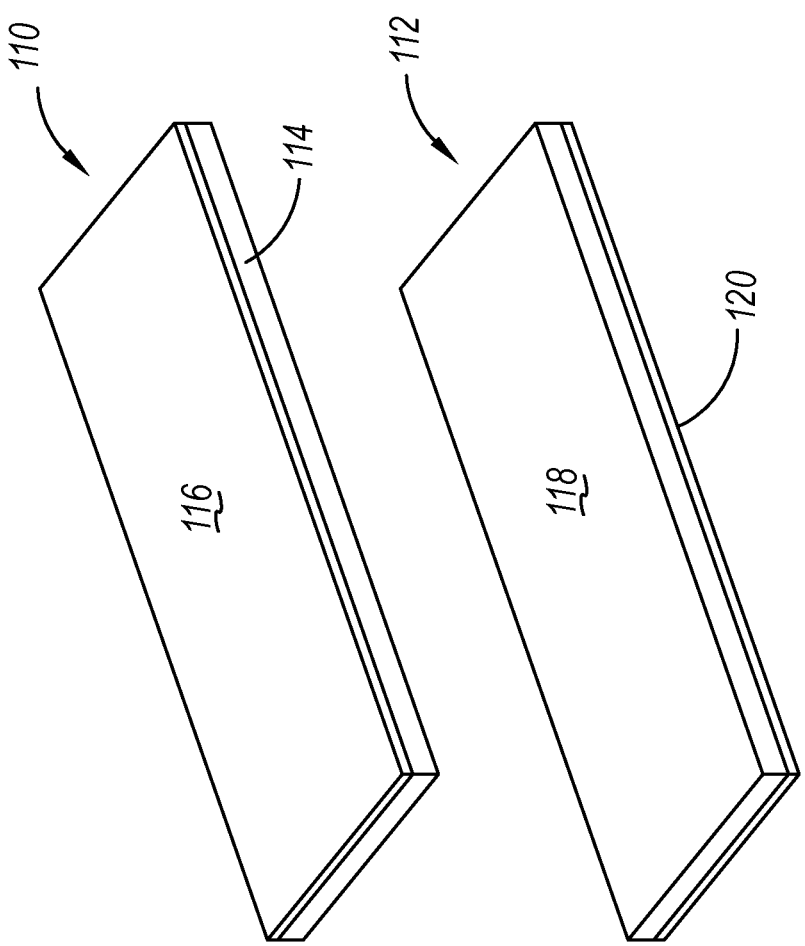
FIG. 8 depicts a perspective view of an exemplary pair of buttress assemblies, each of which may be applied to a jaw of the end effector of FIG. 3.

FIG. 8 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
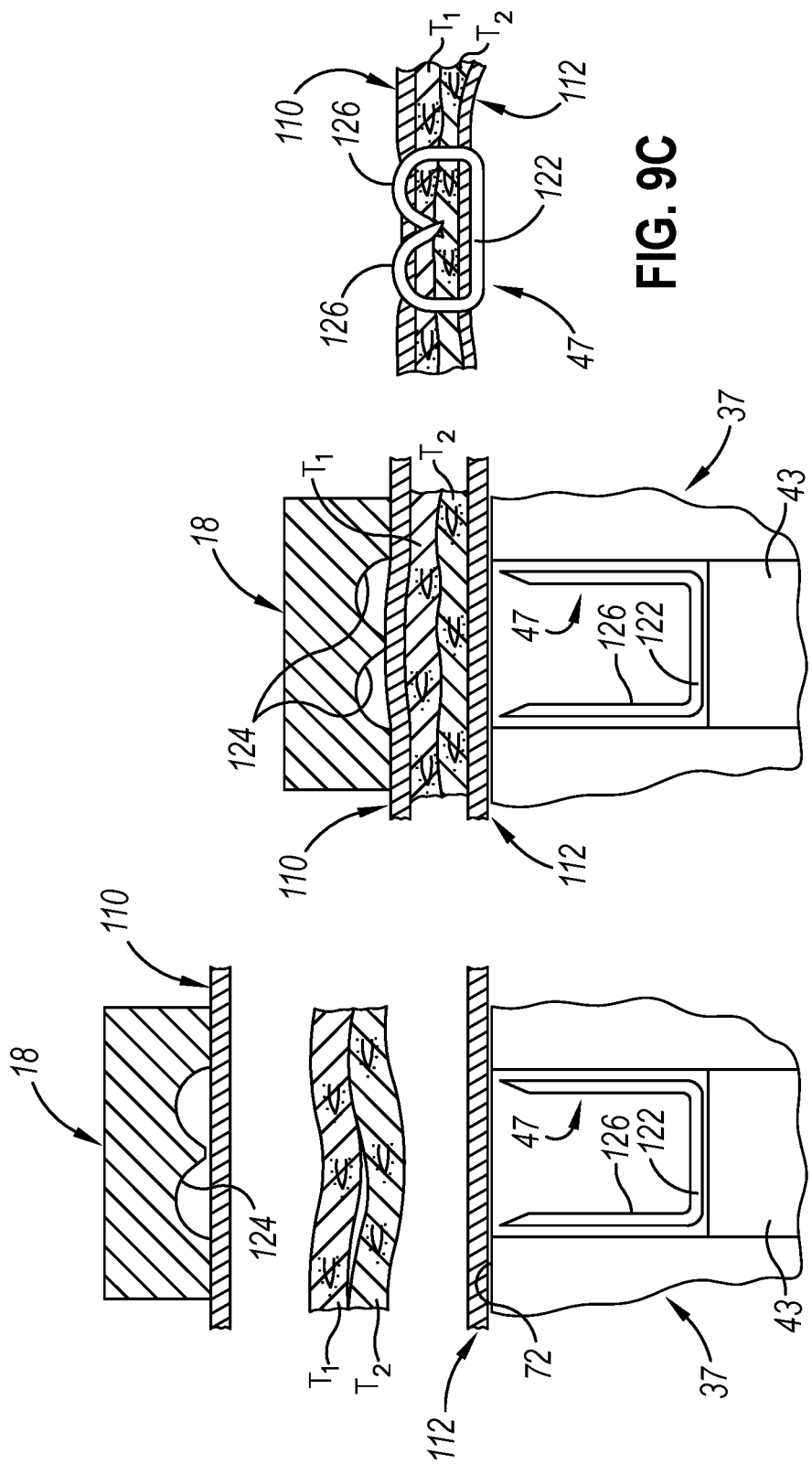
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which end effector (12), which has been loaded with buttress assemblies (110, 112) on its stapling surfaces, is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in open position. Buttress assembly (110) is adhered to underside (424) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
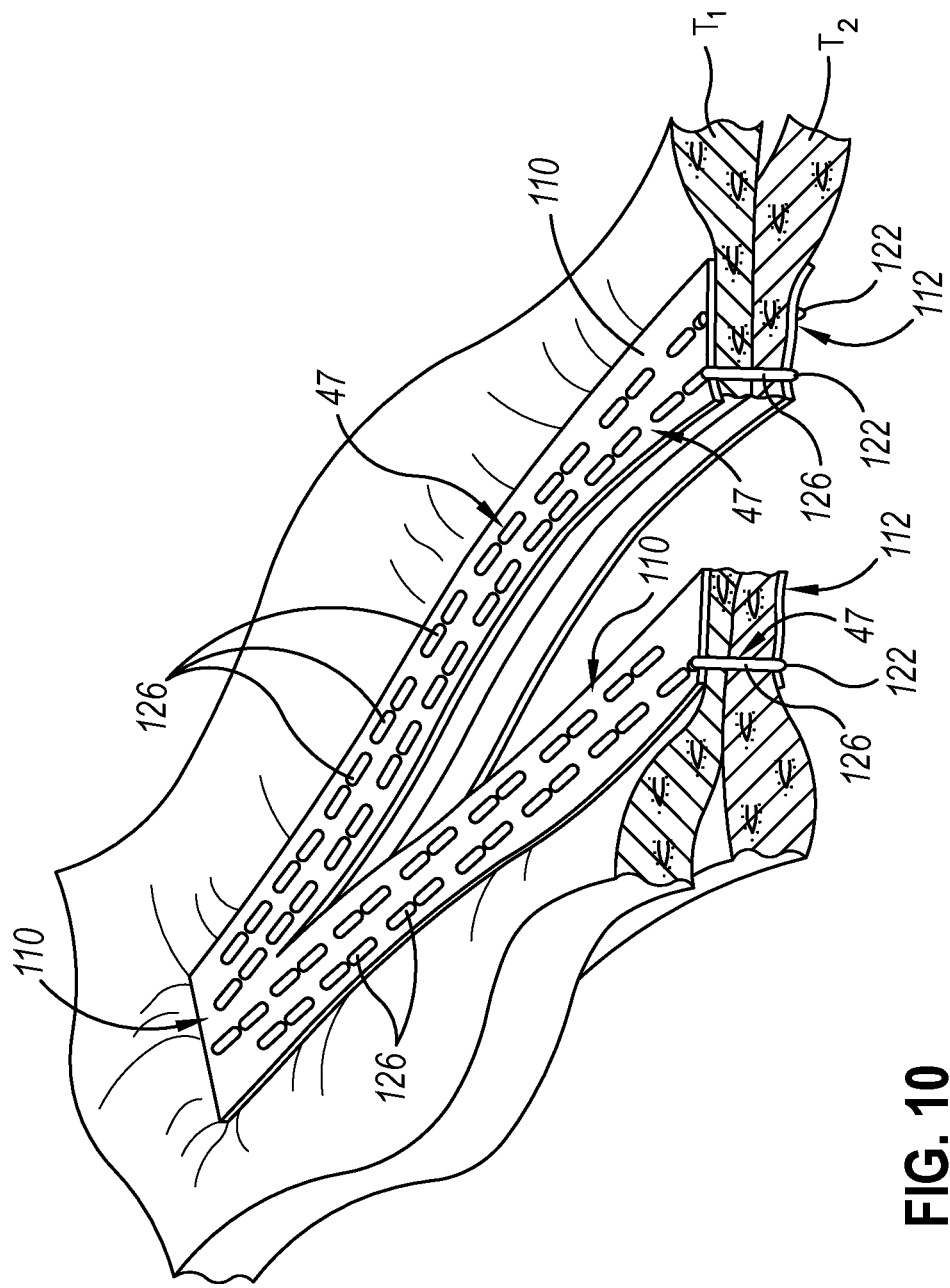
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttress assemblies (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress assemblies (110, 112), separating each buttress assembly (110, 112) into a corresponding pair of sections, such that each section remains secured to a respective severed region of tissue ($T_1$, $T_2$).

C. Exemplary Adjunct Applicator Device with Active Retainer Arms

Figure 11:
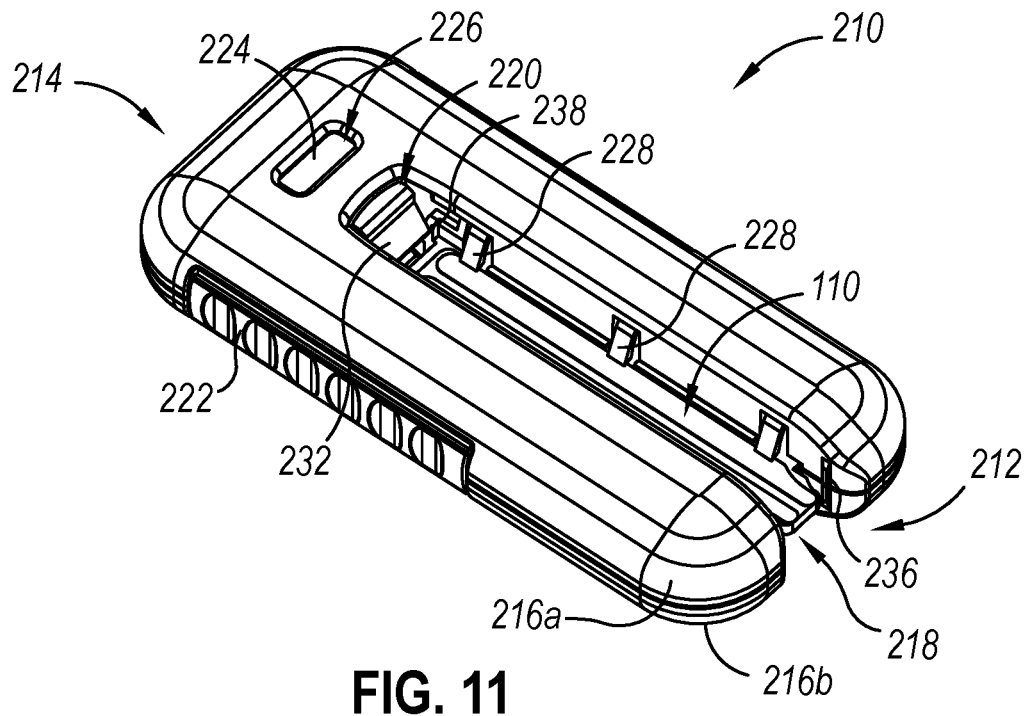
FIG. 11 depicts a perspective view of an exemplary adjunct applicator device that may be used to carry and apply the buttress assemblies of FIG. 8.
Figure 12:
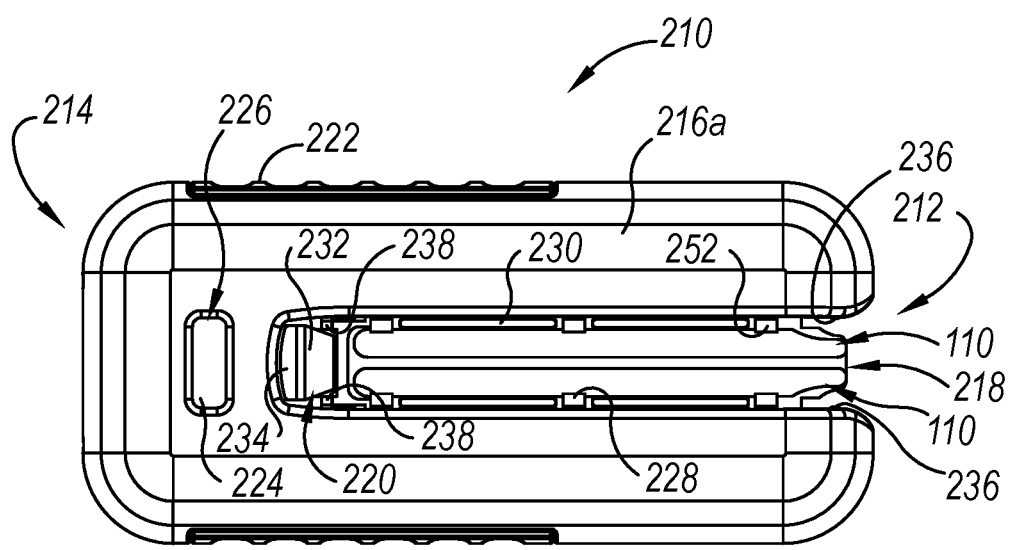
FIG. 12 depicts a top plan view of the adjunct applicator device of FIG. 11.

Because end effector (12) of surgical stapler (10) may be actuated multiple times during a single surgical procedure, it may be desirable to enable an operator to repeatedly and easily load buttress assemblies (110, 112) onto lower jaw and anvil (16, 18) during that single surgical procedure. FIGS. 11-13B show an exemplary adjunct applicator device (210) (also referred to as a "buttress applicator" or a "buttress applier cartridge") that may be used to support, protect, and apply adjunct material, such as buttress assemblies (110, 112), to end effector (12). As best seen in FIGS. 11-12, applicator device (210) of this example comprises an open end (212) and a closed end (214). Open end (212) is configured to receive end effector (12) as will be described in greater detail below. Applicator device (210) further includes a body having a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, outer edges of platform (218) include retention features in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Applicator device (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with applicator device (210).

Figure 13A:
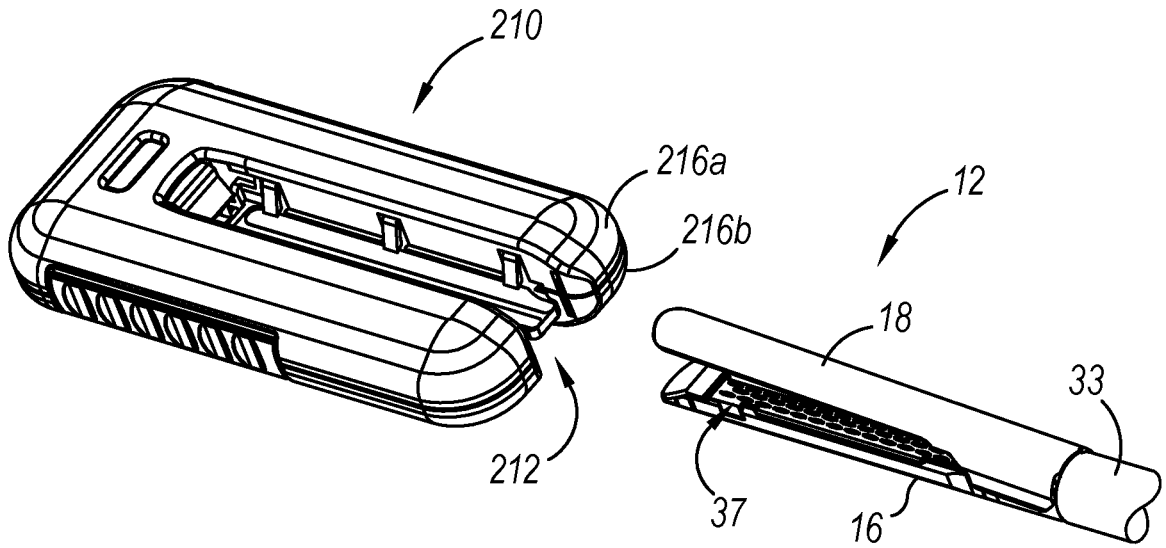
FIG. 13A depicts a perspective view of the end effector of FIG. 3 and the adjunct applicator device of FIG. 11, showing the end effector and the adjunct applicator device being aligned with one another.
Figure 13B:
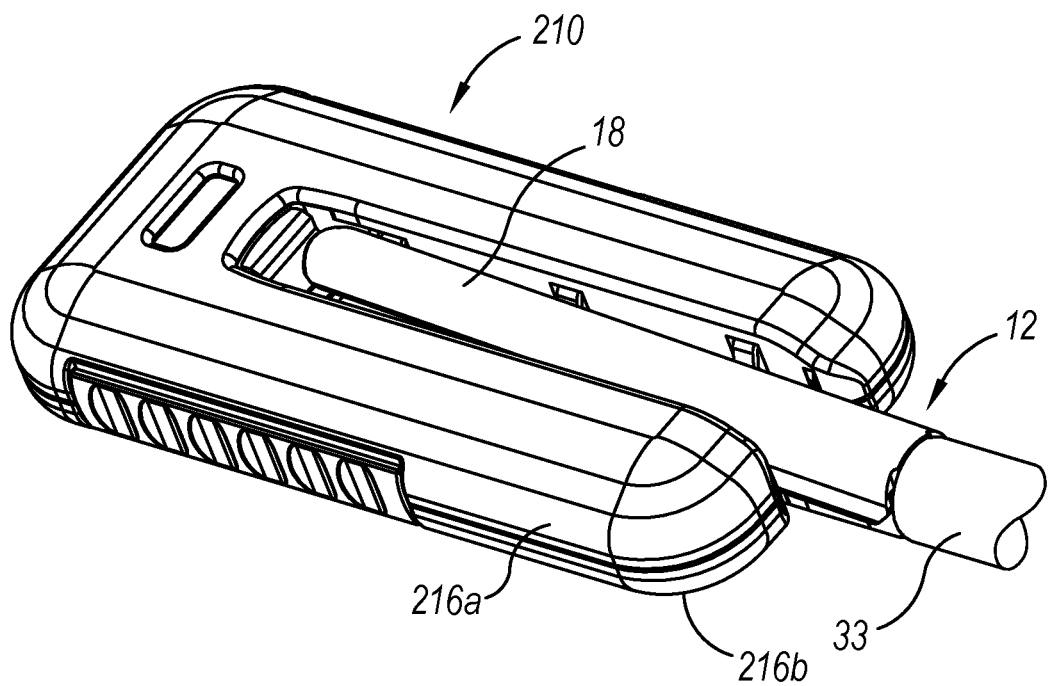
FIG. 13B depicts a perspective view of the end effector of FIG. 3 and the adjunct applicator device of FIG. 11, with the end effectors jaws closed on a platform of the adjunct applicator device.

FIG. 13A shows adjunct applicator device (210) in a configuration where retainer arms (228) are positioned to hold buttress assemblies (110, 112) against platform (218); while FIG. 13B shows applicator device (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use applicator device (210) to load end effector (12), the operator would first position applicator device (210) and end effector (12) such that end effector is aligned with open end (212) of applicator device (210) as shown in FIG. 13A. The operator would then advance end effector (12) distally, and/or advance adjunct applicator device (210) proximally, to position platform (218) and buttress assemblies (110, 112) between anvil (18) and staple cartridge (37) as shown in FIG. 13B. Closure trigger (26) of instrument (10) is then squeezed by the operator to close lower jaw and anvil (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that lower jaw and anvil (16, 18) may be disengaged from platform (218) while buttress assemblies (110, 112) remain adhered to anvil (18) and staple cartridge (37). Adjunct applicator device (210) may be further configured in accordance with any of the disclosures incorporated by reference above.

III. EXEMPLARY END EFFECTOR CLOSURE DEVICES FOR USE WITH ADJUNCT APPLICATOR

In some instances, it may be desirable to apply one or more adjuncts, such as buttress assemblies (110, 112), to the stapling surfaces of surgical stapler end effector (12) without actuating an end effector closure assembly of stapler (10) via closure trigger (26). For instance, variations of stapler (10) that are configured to be mounted to a surgical robot may omit a traditional handle assembly and corresponding operator-actuatable features, such as closure trigger (26) and firing trigger (28), such that traditional actuation of the end effector closure assembly of stapler (10) is controllable only by the surgical robot. Furthermore, in some such instances, an operator may have a need to apply the one or more adjuncts to end effector (12) without activating the surgical robot, for example when stapler (10) is decoupled from the surgical robot or when the surgical robot is in a deactivated state. The exemplary devices described below are configured to directly contact and facilitate closure of end effector (12) onto platform (218) of adjunct applicator device (210), or onto a similar adjunct-carrying structure of other types of adjunct applicator devices, so that one or more adjuncts may be applied to a corresponding one or more stapling surfaces of end effector (12) without traditional actuation of the end effector closure assembly.

A. End Effector Closure Device Having Actuatable Lever

FIGS. 14-19C show an exemplary end effector closure device (300) that is operable to receive and support adjunct applicator device (210) in combination with end effector (12) in an open state, and to directly contact and close end effector jaws (16, 18) onto applicator platform (218) to apply an adjunct, such as a buttress assembly (110, 112), to the stapling surface of one or both jaws (16, 18) without actuation of closure trigger (26). Accordingly, end effector closure device (300) is configured to cooperate with applicator device (210) to define an adjunct applicator system.

Figure 14:
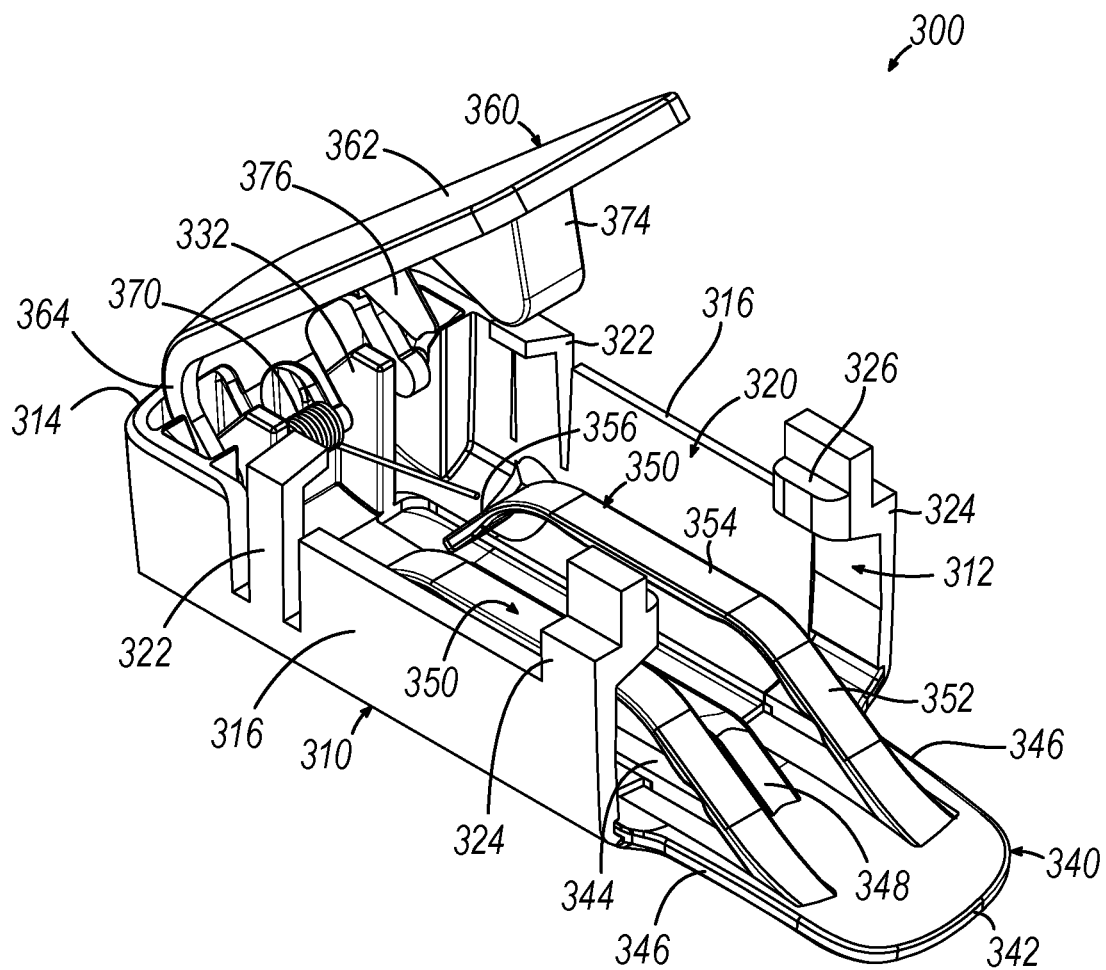
FIG. 14 depicts a perspective view of an exemplary end effector closure device configured for use with the surgical stapler end effector of FIG. 3 and the adjunct applicator device of FIG. 11, showing the end effector closure device in an open state.
Figure 15:
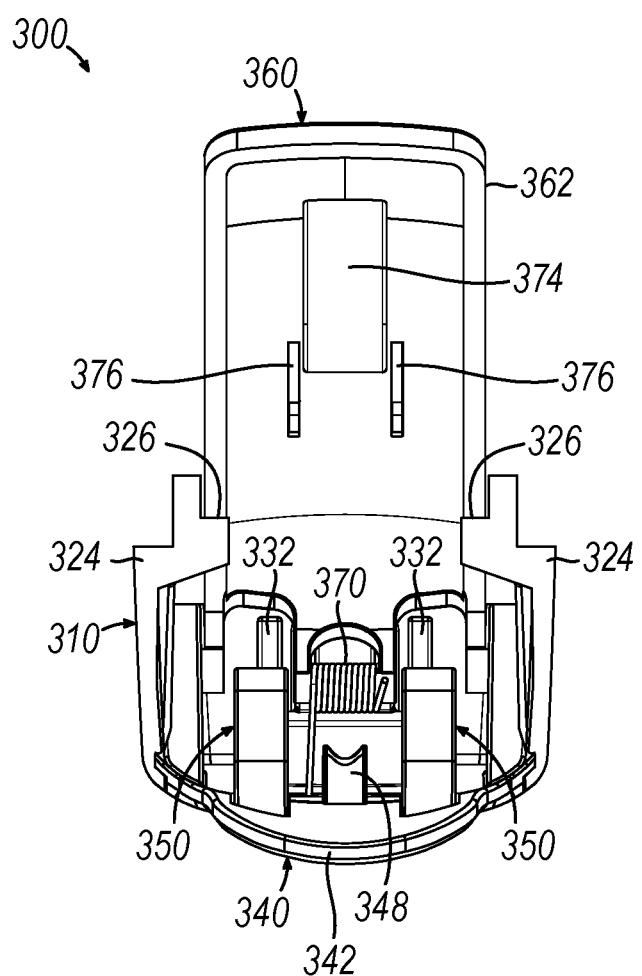
FIG. 15 depicts a front elevational view of the end effector closure device of FIG. 14 in the open state.
Figure 16:
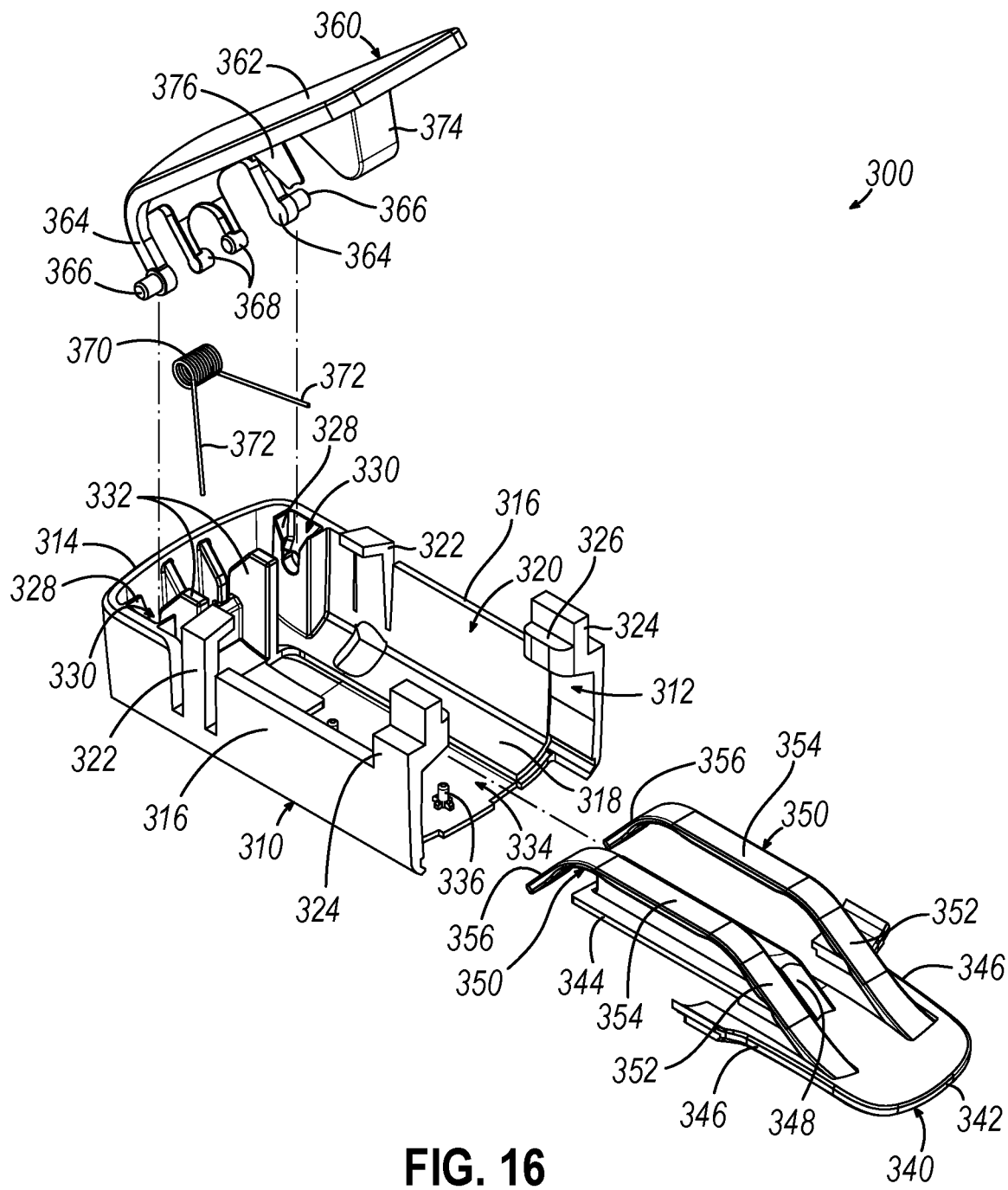
FIG. 16 depicts a disassembled perspective view of the end effector closure device of FIG. 14.

As shown in FIGS. 14-16, end effector closure device (300) includes a lower body having a frame (310) and a support structure (340) configured to support an underside of adjunct applicator device (210), and an upper movable member (also referred to herein as a closure driver) in the form of a lever (360) pivotably coupled with frame (310) in a clamshell-like configuration and movable between a raised open position and a lowered closed position. Frame (310) of the present example is generally rectangular and formed as a unitary structure that includes a proximal end opening (312), a distal end wall (314), and a pair of elongate side walls (316) and a bottom wall (318) extending longitudinally between proximal end opening (312) and distal end wall (314). Distal end wall (314), side walls (316), and bottom wall (318) cooperate to define an interior space of closure device (300) in which adjunct applicator device (210) is configured to be received and supported by support structure (340), as described in greater detail below. Additionally, distal end wall (314) and side walls (316) cooperate to define an upper opening (320) opposed from bottom wall (318) and in which lever (360) is movable to engage an exterior jaw surface of end effector (12).

Frame side walls (316) of end effector closure device (300) include a pair of distal retaining arms (322) configured to overlie a top surface of a distal portion of adjunct applicator device (210), and a pair of proximal retaining arms (324) configured overlie the top surface of a proximal portion of adjunct applicator device (210). Distal and proximal retaining arms (324) cooperate to constrain adjunct applicator device (210) in a vertical direction when applicator device (210) is loaded into closure device (300), for example as shown in FIG. 17B. Each proximal retaining arm (324) includes a lever stop feature in the form of a generally flat stop surface (326) that overlies proximal end opening (312) and is configured to contact an underside of lever (360) in its closed position, for example as shown in FIG. 18C, to thereby limit a range of rotation of lever (360).

A distal end portion of frame (310) includes a pair of pivot support structures (328) each integrated into the distal end of a respective side wall (316) and having an upwardly opening, tapered recess (330) configured to receive a respective pivot post (366) of lever (360), described in greater detail below. A pair of applicator stop members (332) in the form of vertical fins extend upwardly from bottom wall (318) between pivot support structures (328) within the interior space of frame (310). Applicator stop members (332) are configured to abut a distal end of adjunct applicator device (210) and thereby constrain applicator device (210) distally when loaded into closure device (300).

Support structure (340) of end effector closure device (300) is shaped and sized to be seated within a channel (334) formed in bottom wall (318) of frame (310) and is permanently affixed to frame (310) via a plurality of coupling protrusions (336) extending upwardly from frame (310) within channel (334). Coupling protrusions (336) may be configured to couple with support structure (340) via press-fit, snap-fit, or heat staking, for example, though it will be appreciated that support structure (340) may be affixed to frame (310) in a variety of other manners readily apparent to those of ordinary skill in the art in view of the teachings herein.

Support structure (340) of the present example is formed as a single unitary structure that includes a base (342) having a central tongue (344) shaped to be seated within channel (334) of frame (310), and a pair of side arms (346) each spaced apart laterally from a respective side of central tongue (344) and having a free distal end configured to mate with a respective proximal edge feature of frame (310), for example with a tongue-and-groove interface. An end effector jaw support feature in the form of an elongate rail (348) protrudes upwardly from and extends longitudinally along central tongue (344). Elongate rail (348) includes a ramped proximal end and a concave upper surface that enables elongate rail (348) to contact and support an exterior surface of a jaw (16, 18) of end effector (12) when lever (360) is closed onto end effector (12), for example as shown in FIGS. 18C and 19C described below.

Support structure (340) further includes a pair of elongate applicator support members in the form of leaf springs (350) configured to contact and support an underside of adjunct applicator device (210) when loaded into end effector closure device (300). Each leaf spring (350) extends distally from a proximal end of base (342) along a respective side of support structure (340) and includes an upwardly sloped proximal section (352), a generally horizontal medial section (354), and a downwardly sloped distal section (356) that terminates at a rounded free end configured to be spaced above bottom wall (318) of frame (310). Each leaf spring (350) is configured to function as a resilient support member that resiliently deflects downwardly toward bottom wall (318) of frame (310) when adjunct applicator device (210) is inserted distally into end effector closure device (300), and thus urges applicator device (210) upwardly toward lever (360) and away from bottom wall (318) to thereby position applicator device (210) appropriately so that end effector (12) may be received into the interior space of closure device (300) and positioned about platform (218), as described in greater detail below. While two applicator support members in the form of leaf springs (350) are shown in the present version of closure device (300), it will be appreciated that various other configurations and quantities of applicator support members may be provided in other versions of closure device (300).

Lever (360) of end effector closure device (300) includes lever body (362) having a free proximal end and a distal end from which a pair of pivot arms (364) and a pair of spring support arms (368) extend downwardly to provide lever (360) with a generally L-like shape. Each pivot arm (364) includes a pivot post (366) configured to be received by a respective pivot support structure (328) of frame (310) to pivotably couple the distal end of lever (360) with the distal end of frame (310) such that lever (360) is pivotable relative to frame (310) between a raised open position (see FIGS. 18A and 18B) and a lowered closed position (see FIG. 18C). Spring support arms (368) are positioned between pivot arms (364) and are configured to cooperate to support a resilient member in the form of a torsion spring (370) having a pair of spring legs (372) configured to contact lever (360) and frame (310) to bias lever (360) toward its raised open position.

Lever (360) further includes a camming protrusion (374) that extends downwardly from an underside of lever (360) and is tapered with a rounded free end. Camming protrusion (374) is configured to cammingly engage an exterior surface of a jaw (16, 18) of end effector (12) to close end effector (12) onto platform (218) of adjunct applicator device (210) when lever (360) is closed by an operator. Lever (360) further includes a pair of alignment tabs (376) that extend downwardly from the underside of lever (360) at a location distal to camming protrusion (374). As shown best in FIG.

15, alignment tabs (376) are spaced apart from one another by a lateral width that is slightly greater than a maximum lateral width of jaws (16, 18) of end effector (12). Accordingly, alignment tabs (376) are configured to receive a jaw (16, 18) therebetween and thereby promote lateral alignment of jaws (16, 18) with adjunct applicator device (210) and with end effector closure device (300) as lever (360) is actuated to its closed position to close end effector (12) onto adjunct applicator device (210). In some versions, the free end of each alignment tab (376) may be configured to cammingly engage a respective adjunct retaining arm (228) of applicator device (210) to facilitate release of a corresponding adjunct from platform (218). While lever (360) of the present version is shown having an end effector closure feature in the form of camming protrusion (374) and an end effector alignment feature in the form of alignment tabs (376), it will be appreciated that various other configurations and quantities of end effector closure and alignment features may be provided in other versions. Furthermore, while end effector closure device (300) of the present version is shown having a closure member in the form of pivotable lever (360), it will be appreciated that closure device (300) of other versions may have a closure member of various other types, such as a translatable closure member.

Figure 17A:
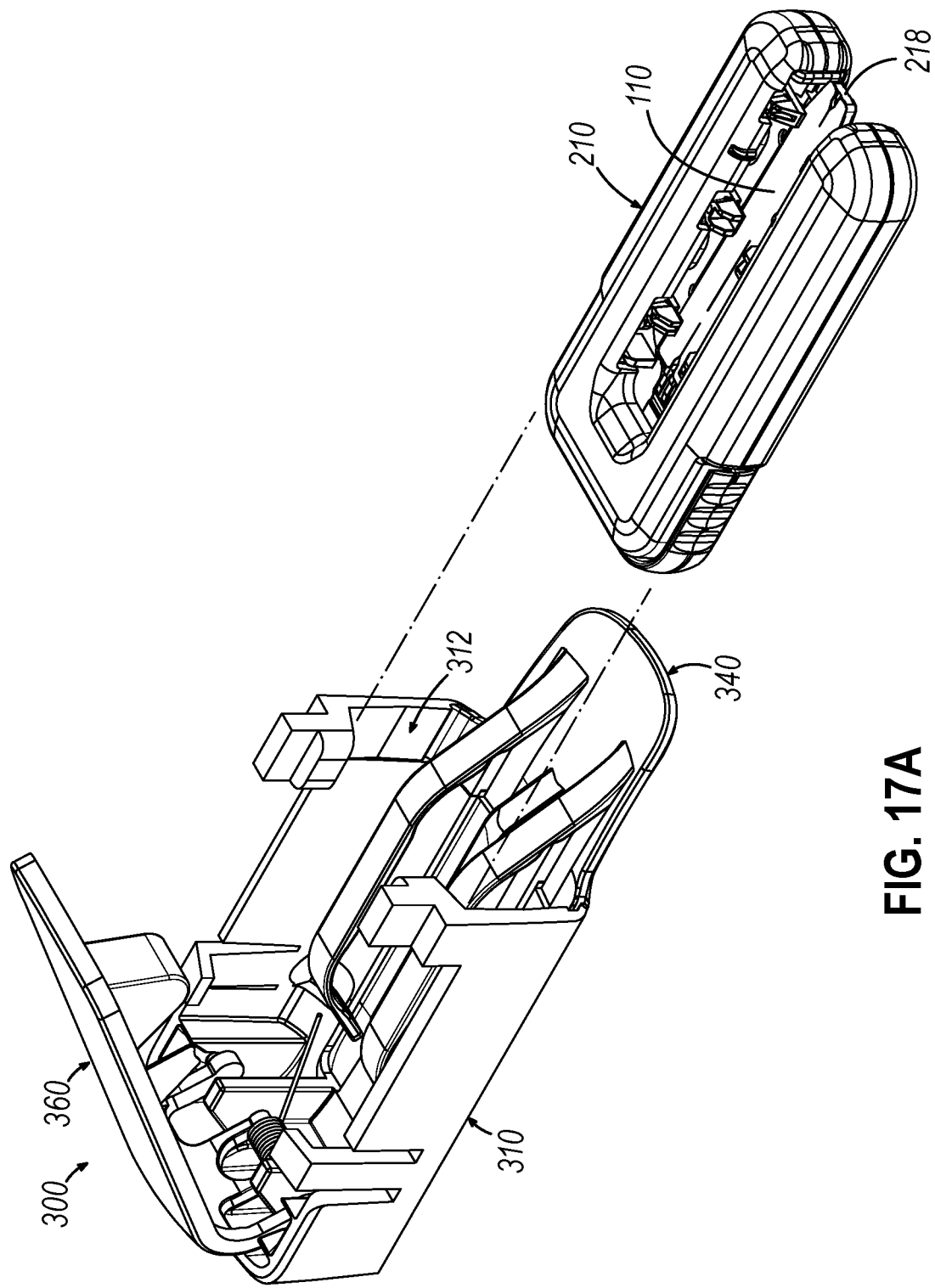
FIG. 17A depicts a perspective view of the end effector closure device of FIG. 14 and the adjunct applicator device of FIG. 11, showing the adjunct applicator device separated from and aligned with an open proximal end of the end effector closure device.
Figure 17B:
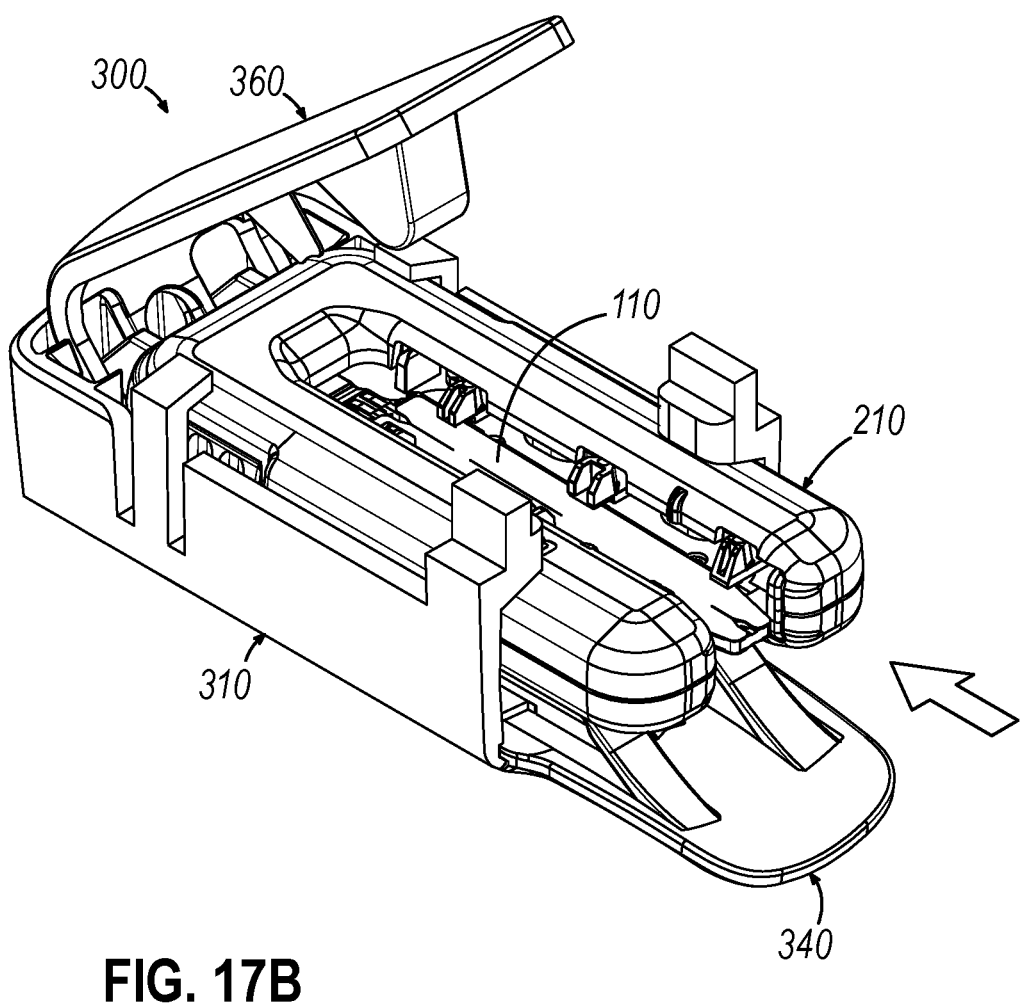
FIG. 17B depicts a perspective view of the end effector closure device of FIG. 14 and the adjunct applicator device of FIG. 11, showing the adjunct applicator device having been inserted distally into an interior space of the end effector closure device to define an adjunct applicator system.

As shown in FIGS. 17A-17B, a distal end of adjunct applicator device (210), preloaded with buttress assemblies (110, 112) or any other suitable adjunct type on platform (218), is aligned with proximal end opening (312) of end effector closure device (300), with lever (360) resiliently biased into its raised open position. Adjunct applicator device (210) is then inserted distally through proximal end opening (312) and into the interior space closure device (300) until the distal end of applicator device (210) abuts applicator stop members (332) of frame (310). In doing so, applicator device (210) slides over leaf springs (350), thus causing leaf springs (350) to resiliently deflect downwardly toward bottom wall (318) of frame (310) so that leaf springs (350) urge applicator device upwardly toward lever (360) and against the undersides of proximal and distal retaining arms (322) of frame (310). Applicator device (210) and closure device (300) thus define an adjunct applicator system now ready to receive end effector (12).

Figure 18A:
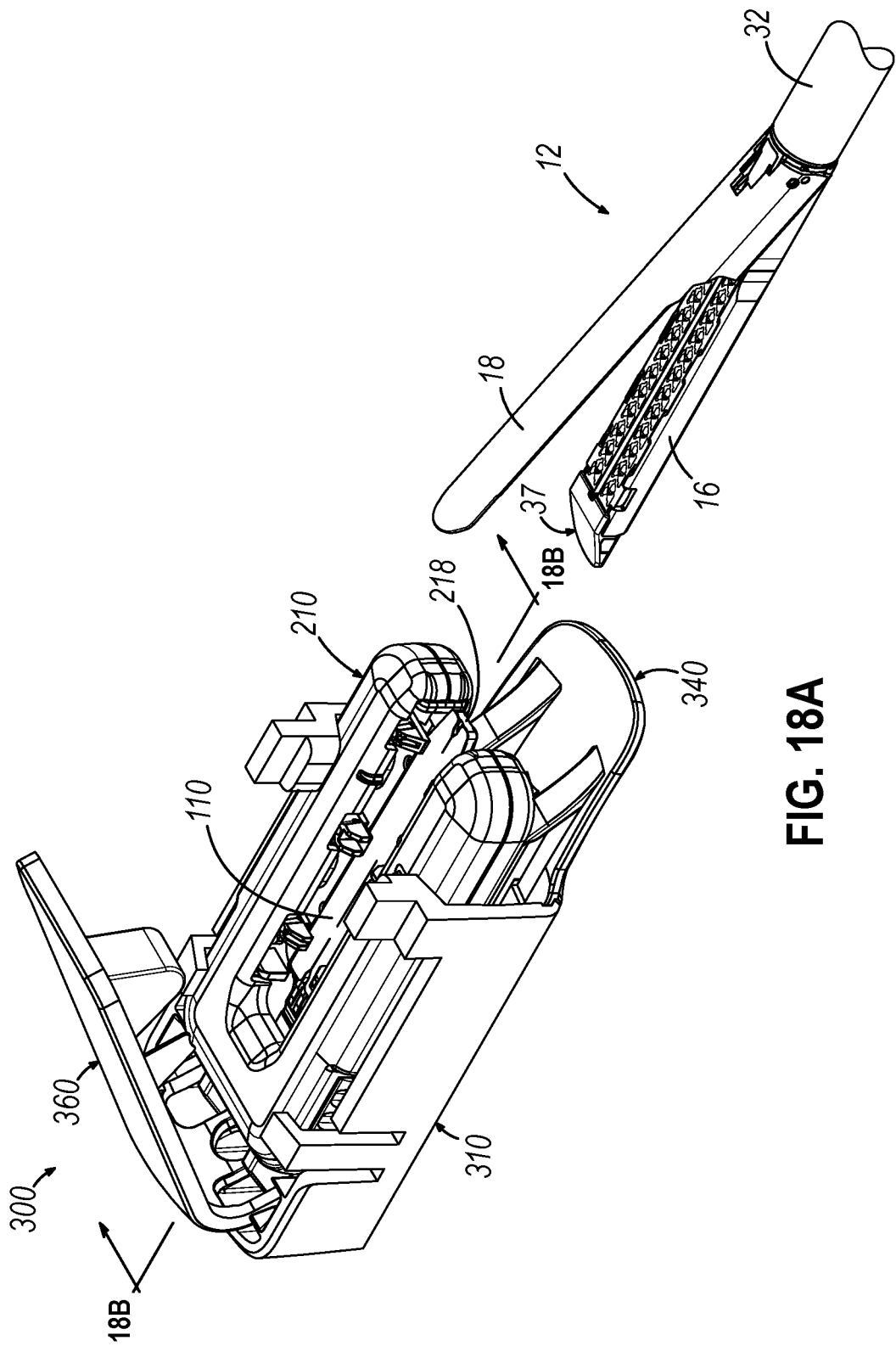
FIG. 18A depicts a perspective view of the adjunct applicator system of FIG. 17B separated distally from and aligned with the end effector of FIG. 3, showing the end effector in an open state and in a first rotational orientation relative to the adjunct applicator system.
Figure 18B:
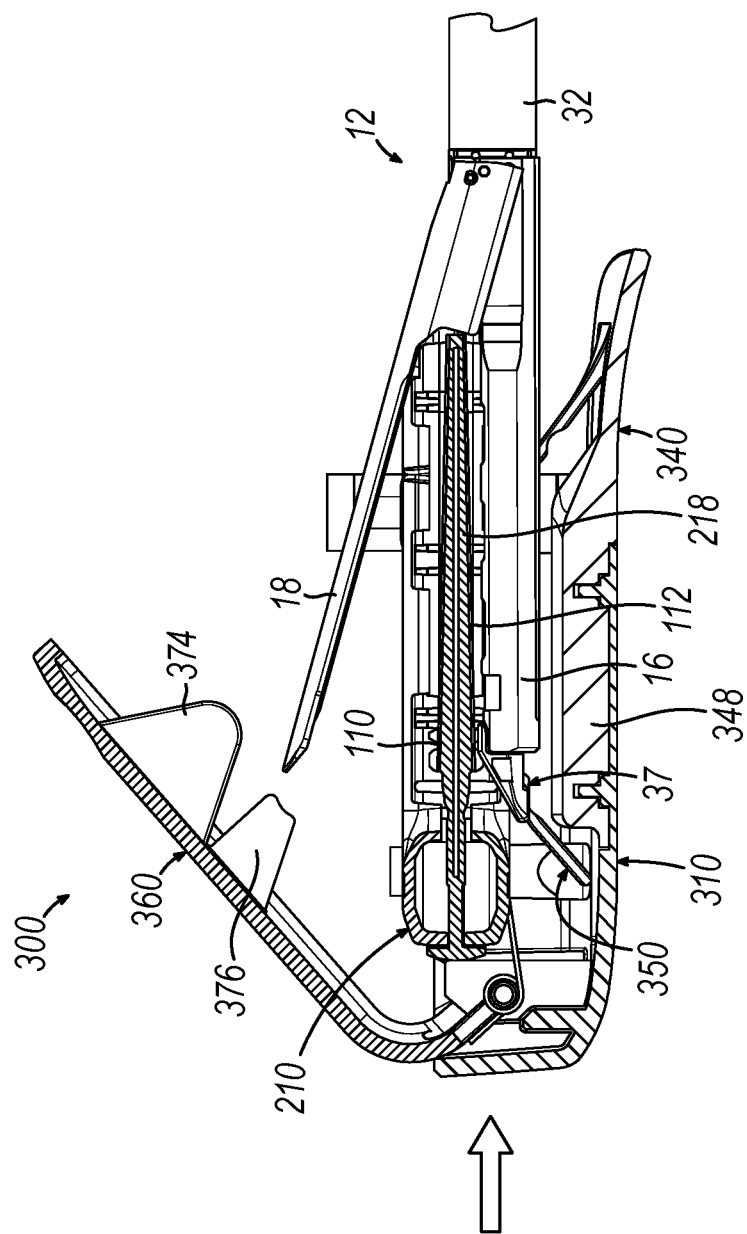
FIG. 18B depicts a partial cross-sectional side view of the adjunct applicator system and the end effector of FIG. 18A, taken along section line 18B-18B of FIG. 18A, showing the end effector closure device and the end effector in open states after the adjunct applicator system has been advanced proximally so that a platform of the adjunct applicator device is received between the jaws of the end effector.
Figure 18C:
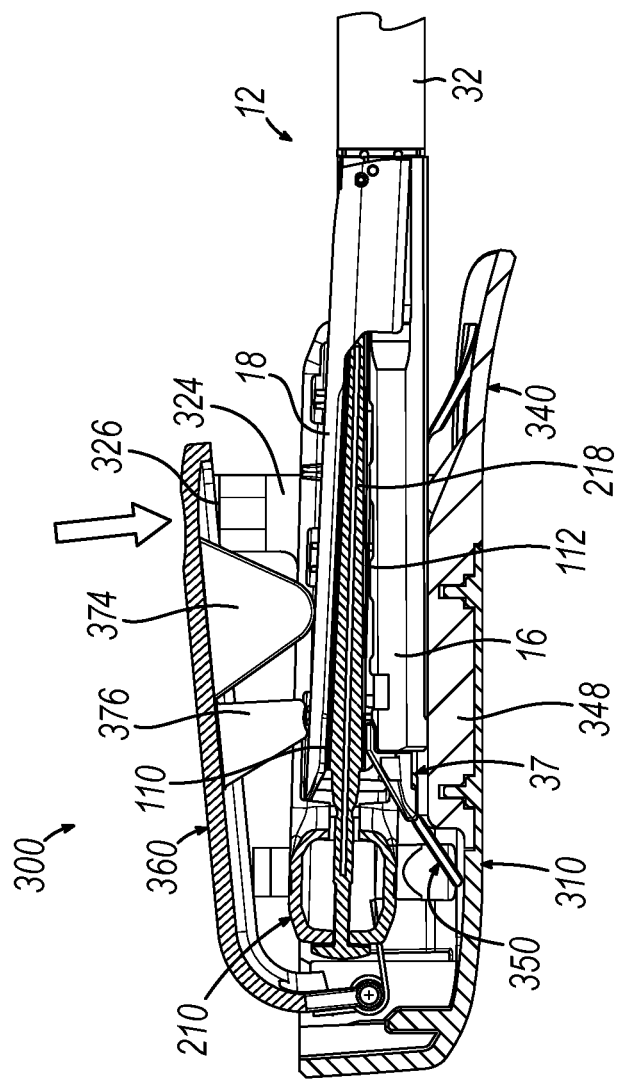
FIG. 18C depicts a partial cross-sectional side view of the adjunct applicator system and the end effector of FIG. 18B, showing the end effector having been actuated to a closed state onto the platform of the adjunct applicator device in response to closure of a closure member of the end effector closure device so that a pair of adjuncts are applied to the stapling surfaces of the end effector jaws.
Figure 18D:
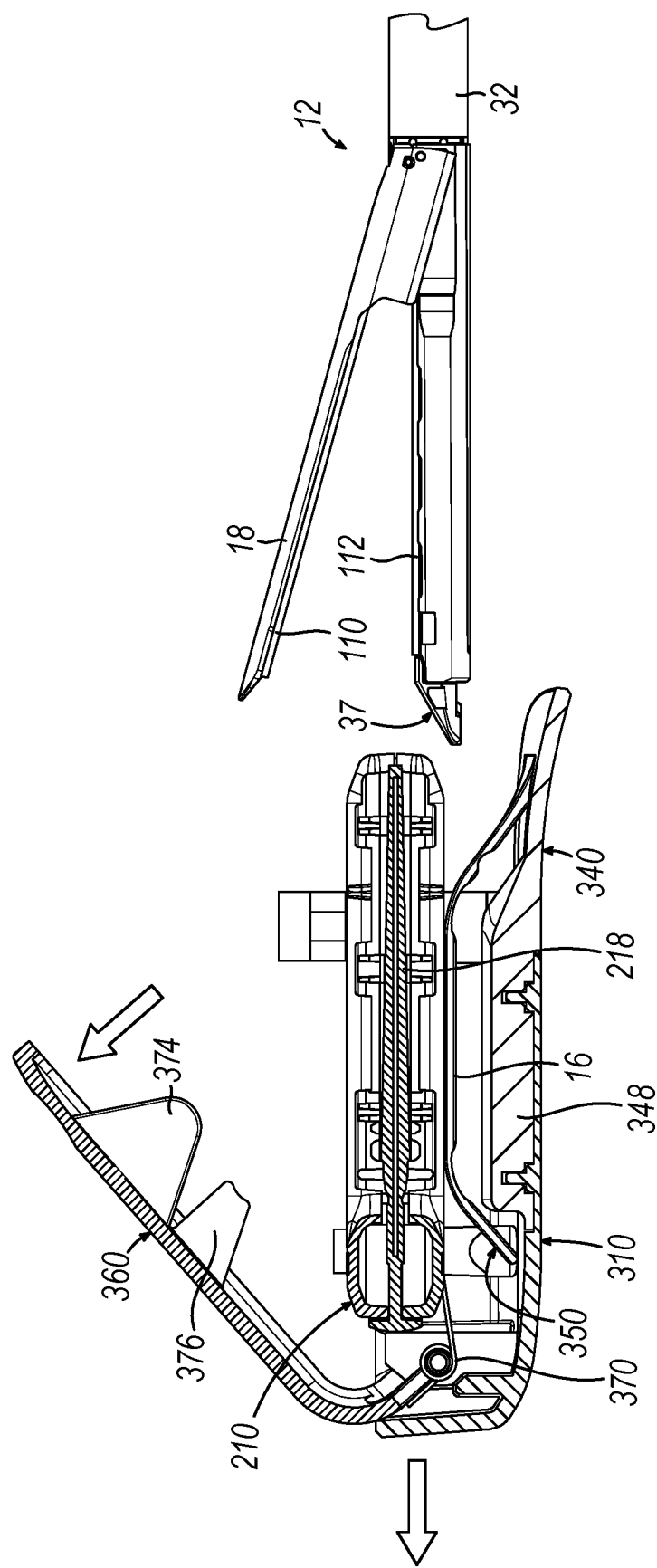
FIG. 18D depicts a partial cross-sectional side view of the adjunct applicator system and the end effector of FIG. 18C, showing the end effector having been released from the adjunct applicator system and returned to the open state with the adjuncts applied to its jaws in response to re-opening of the closure member of the end effector closure device and distal withdrawal of the adjunct applicator system from the end effector.

As shown in FIG. 18A, end effector (12) is positioned in an "anvil-up" rotational orientation relative to end effector closure device (300) such that anvil jaw (18) is oriented toward lever (360) and cartridge jaw (16) is oriented toward frame (310). As shown in FIG. 18B, closure device (300) is advanced proximally toward end effector (12), or alternatively end effector (12) is advanced distally toward closure device (300), so that end effector (12) in the open state is received into the interior space defined by frame (310) and lever (360) where anvil jaw (18) faces an upper side of platform (218) and cartridge jaw (16) faces an lower side of platform (218). Leaf springs (350) of support structure (340) are spaced apart laterally by a distance sufficient to receive cartridge jaw (16) therebetween without contact.

As shown in FIG. 18C, with end effector (12) positioned within end effector closure device (300), lever (360) is closed by an operator by depressing lever (360) at its proximal end so that camming protrusion (374) contacts an exterior surface of anvil jaw (18) to force anvil jaw (18) toward platform (218). Simultaneously, elongate rail (348) of support structure (340) contacts an exterior surface of cartridge jaw (16) to force cartridge jaw (16) toward platform (218). Additionally, during closure of lever (360) adjunct applicator device (210) may be permitted to move vertically within and relative to closure device (300) via resilient deflect of leaf springs (350) relative to frame (310) to facilitate closure of end effector (12) onto platform (218). When lever (360) has reached its fully closed position in which the underside of lever (360) abuts lever stop surfaces (326) of proximal retaining arms (324), end effector (12) is fully closed onto platform (218) of adjunct applicator device (210) such that buttress assemblies (110, 112) are released from platform (218) and adhere to the stapling surfaces of jaws (16, 18). In this manner, stop surfaces (326) may function as a force limiting feature configured to limit the force that closure device exerts on end effector jaws when lever is closed. Additionally, the geometries of camming protrusion, elongate rail, and or leaf springs may be tuned so that closure device exerts a predetermined closure force on end effector jaws when lever is fully closed.

Though not shown, proximal retaining arms (324) may further include a latch feature configured to engage with the proximal end of lever (360) in the fully closed position to provide audible and/or tactile feedback to the operator that the fully closed position has been achieved. Optionally, such latch feature may be configured to releasably maintain lever (360) in the closed position, for example to ensure complete adhesive of buttress assemblies (110, 112) to end effector jaws (16, 18). Once the operator is satisfied that buttress assemblies (110, 112) have been applied to end effector (12), the operator may release pressure from lever (360) to permit lever (360) to return to its raised open position via the resilient bias of torsion spring (370). End effector (12) is also resiliently biased toward its open position such that the re-opening of lever (360) simultaneously permits the re-opening of end effector (12). The combination of closure device (300) and applicator device (210) may then be withdrawn distally from end effector (12), leaving end effector (12) in an open state with buttress assemblies (110, 112) applied to its stapling surfaces.

Figure 19A:
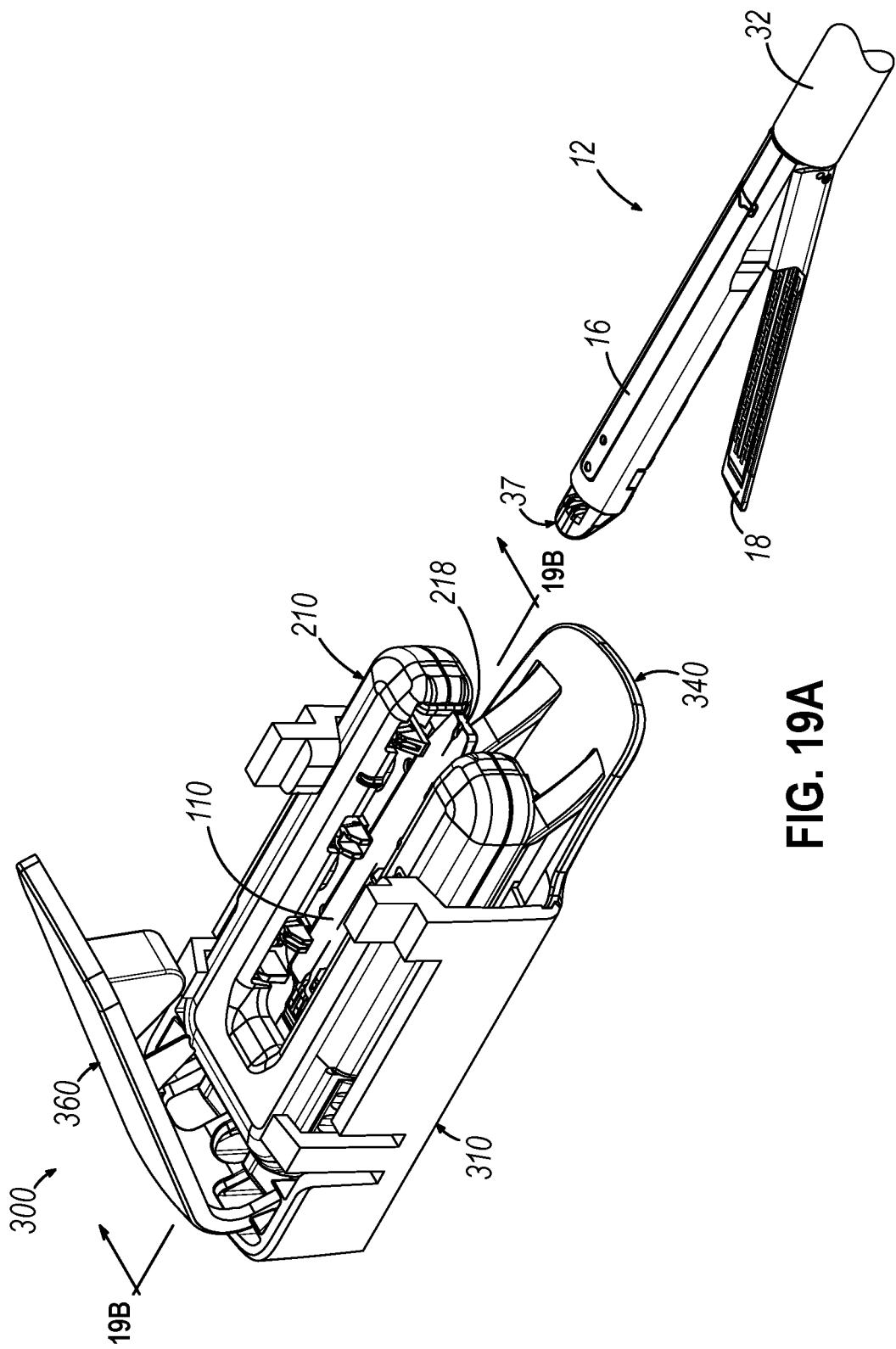
FIG. 19A depicts a perspective view of the adjunct applicator system of FIG. 17B separated distally from and aligned with the end effector of FIG. 3, showing the end effector in an open state and in a second rotational orientation relative to the adjunct applicator system.
Figure 19B:
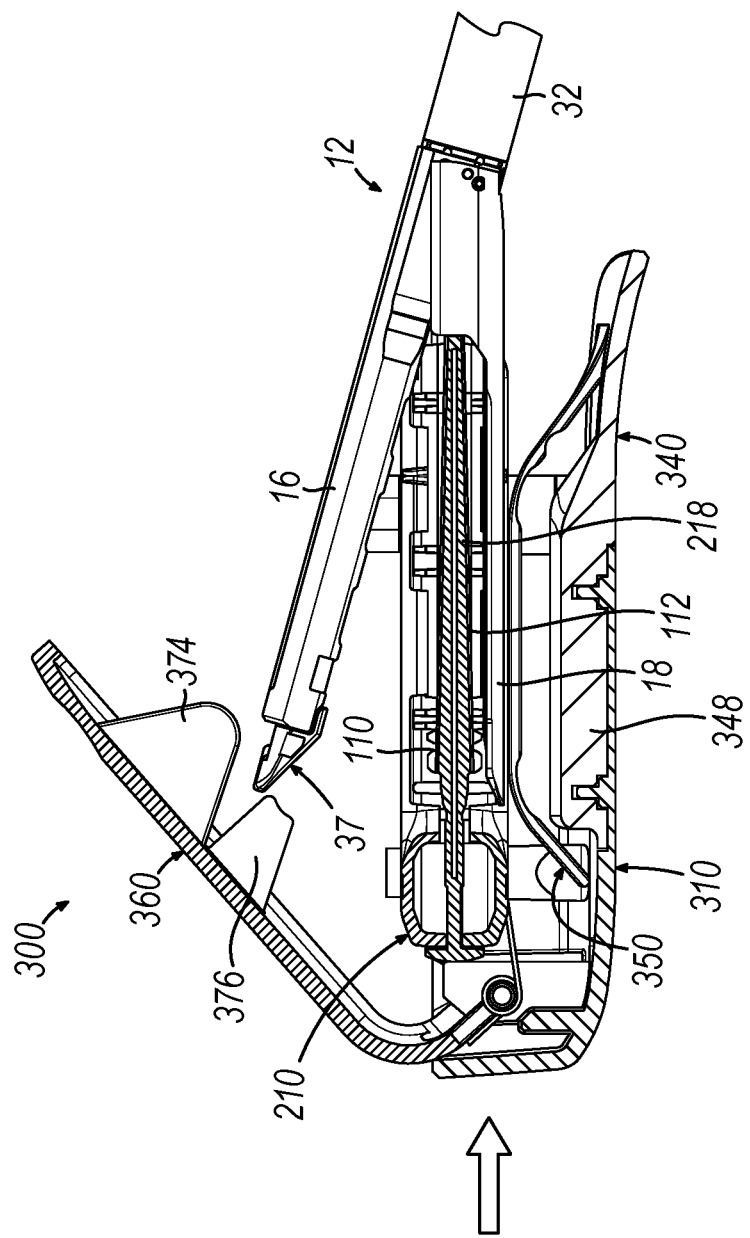
FIG. 19B depicts a partial cross-sectional side view of the adjunct applicator system and the end effector of FIG. 19A, taken along section line 19B-19B of FIG. 19A, showing the end effector closure device and the end effector in open states after the adjunct applicator system has been advanced proximally so that the platform of the adjunct applicator device is received between the jaws of the end effector.

FIGS. 19A-19C show an exemplary alternative method of using end effector closure device (300) and adjunct applicator device (210) with end effector (12) where end effector (12) is positioned in an "anvil-down" rotational orientation relative to closure device (300) such that anvil jaw (18) is oriented toward frame (310) and cartridge jaw (16) is oriented toward lever (360). As shown in FIGS. 19A-19B, end effector (12) is positioned within the interior space of closure device (300) so that platform (218) is positioned between the stapling surfaces of jaws (16, 18). As shown in FIG. 19C, lever (360) is then closed to thereby close jaws (16, 18) onto platform (218) so that buttress assemblies (110, 112) adhere to the stapling surfaces. In this case, camming protrusion (374) of lever (360) forces cartridge jaw (16) toward the upper side of platform (218) and elongate rail (348) of support structure (340) forces anvil jaw (18) toward the lower side of platform (218). Accordingly, it will be appreciated that closure device (300) and applicator device (210) may be used effectively with end effector (12) in either an anvil-up or an anvil-down rotational orientation.

B. End Effector Closure Device Having Scissor-Like Handle

Figure 20:
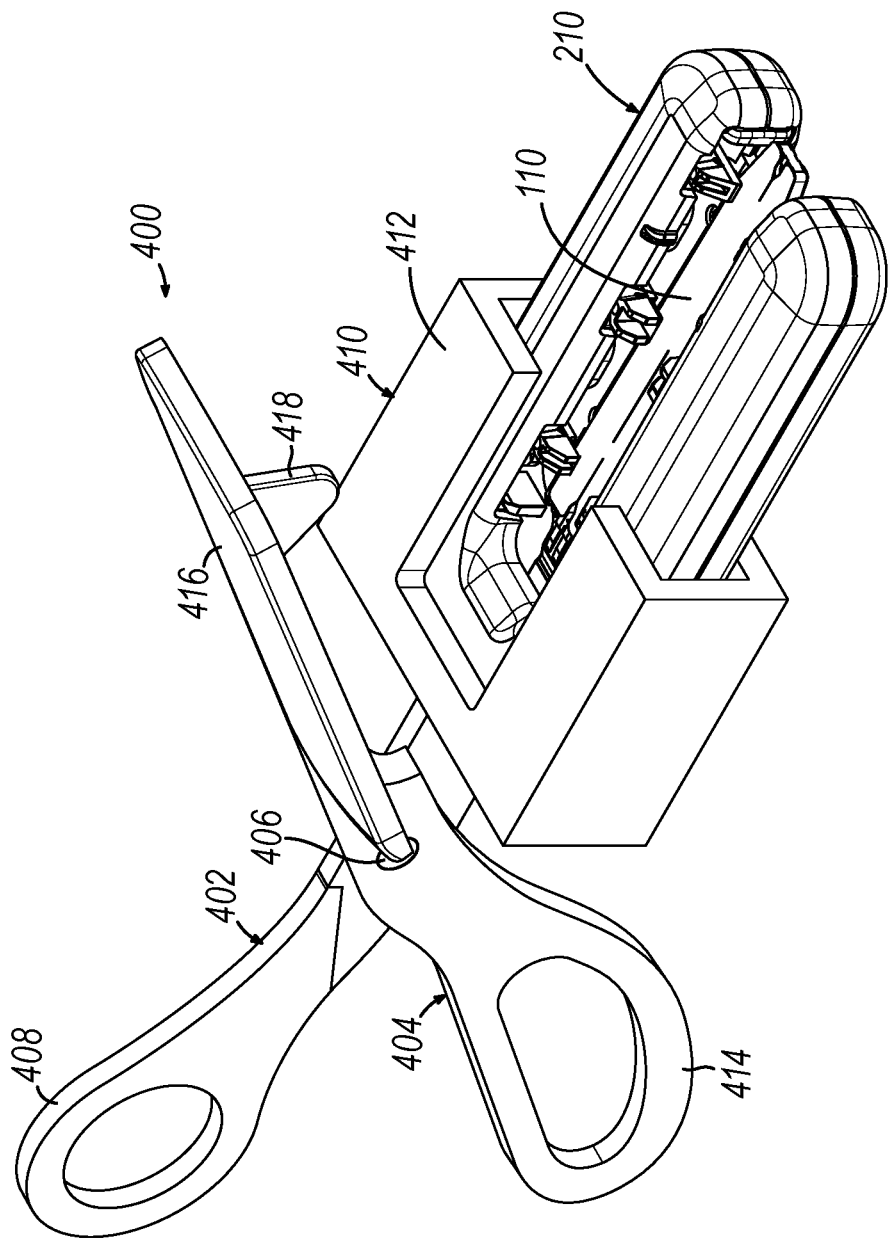
FIG. 20 depicts a perspective view of another exemplary end effector closure device in combination with the adjunct applicator device of FIG. 11 to define another exemplary adjunct applicator system, showing the end effector closure device in an open state.

FIG. 20 shows another exemplary end effector closure device (400) that is operable to receive and support adjunct applicator device (210) and to close end effector (12) onto platform (218) of applicator device (210) to apply buttress assemblies (110, 112), or adjuncts of another type, to the stapling surfaces of end effector jaws (16, 18). Closure device (400) of the present example has a scissor-like configuration that includes a first elongate member (402) and second elongate member (404) pivotably coupled together with a pivot pin (406). First elongate member (402) includes a first proximal handle feature (408) configured to receive a thumb of an operator, and a first distal jaw (410) having a housing (412) configured to receive and support at least a distal portion of adjunct applicator device (210). Second elongate member (404) includes a second proximal handle feature (414) configured to receive two or more fingers of an operator, and a second distal jaw (416) having a camming protrusion (418) similar to camming protrusion (374) described above.

Figure 21A:
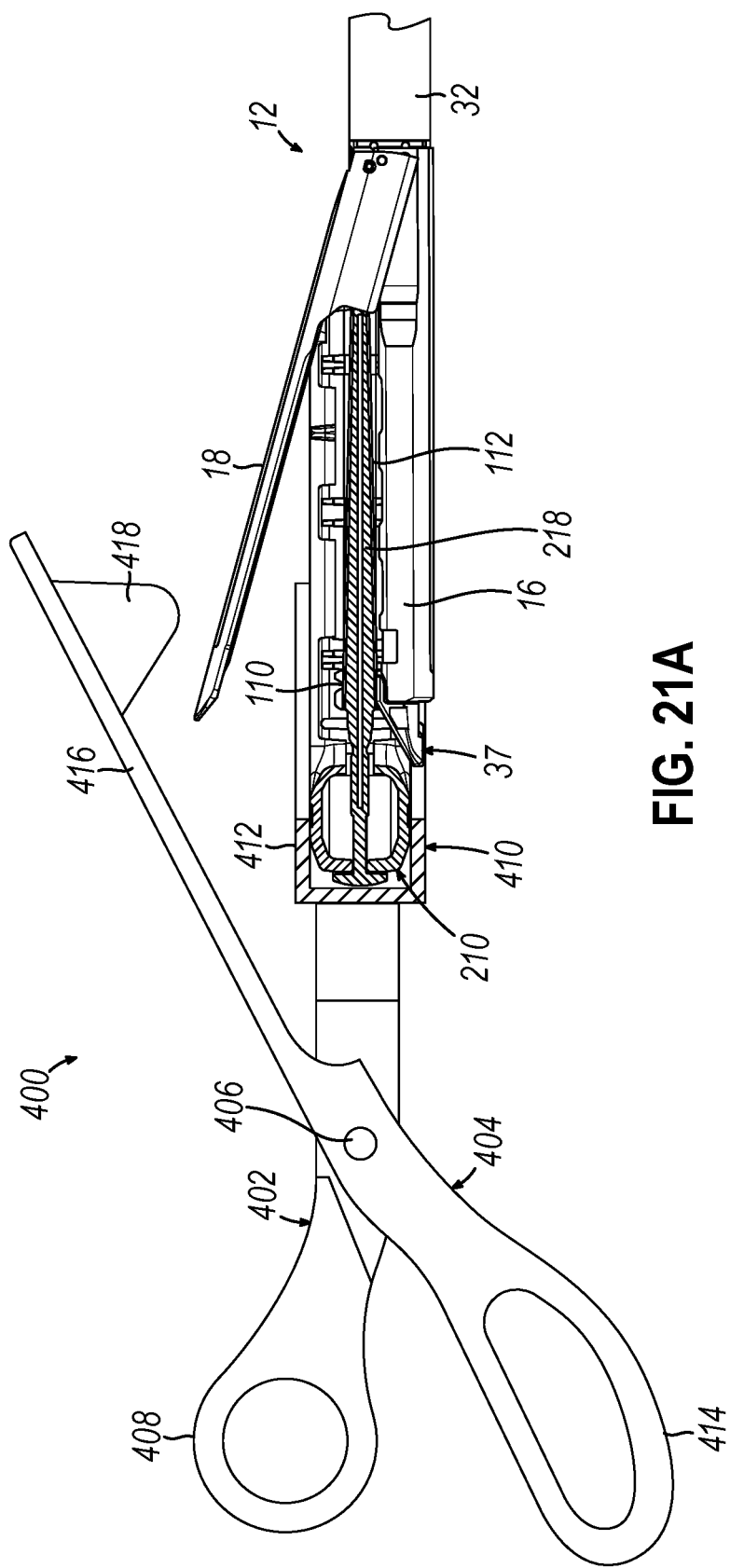
FIG. 21A depicts a partial cross-sectional side view of the adjunct applicator system of FIG. 20, showing the adjunct applicator system having been advanced proximally relative to the end effector of FIG. 3 in an open state so that the platform of the adjunct applicator device is positioned between the jaws of the end effector.
Figure 21B:
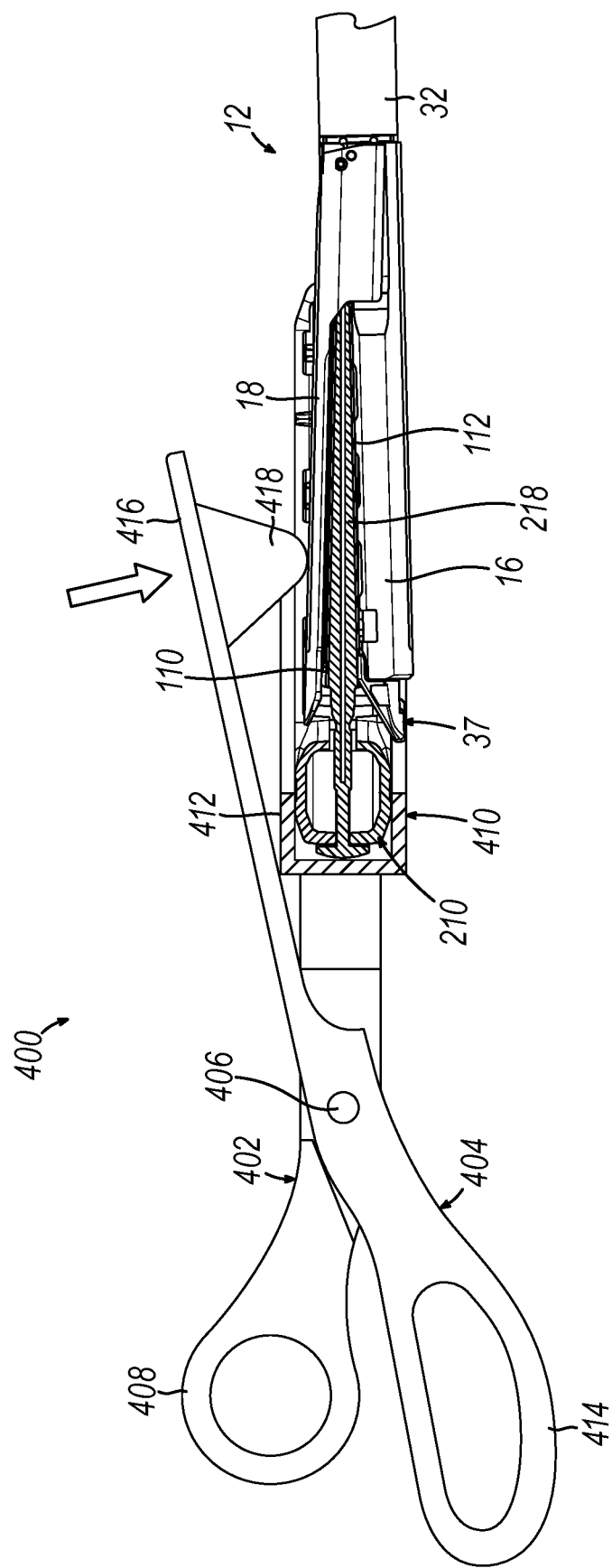
FIG. 21B depicts a partial cross-sectional side view of the adjunct applicator system of FIG. 21A, showing a closure member of the end effector closure device having been actuated to a closed state to close the end effector onto the platform of the adjunct applicator device to apply a pair of adjuncts to the stapling surfaces of the end effector jaws.

As shown FIGS. 21A-21B, end effector (12) is positioned relative to end effector closure device (400) and adjunct applicator device (210) such that a jaw, shown as cartridge jaw (16) in the present example, is inserted in a space between applicator platform (218) and a bottom wall of housing (412) of closure device (400), thereby anchoring an underside of jaw (16) against housing (412). Second elongate member (404) is then pivotably actuated relative to first elongate member (402) to close jaws (16, 18) onto platform (218) to apply buttress assemblies (110, 112) to the stapling surfaces of jaws (16, 18).

End effector closure device (400) may include one or more force limiting features configured to limit the closure force exerted by closure device (400) on end effector jaws (16, 18) when closure device (400) is fully closed. By way of example only, one or more of elongate members (402, 404) may be configured to deflect in response to a predetermined closure force.

C. End Effector Closure Device Having Translatable Sleeve

Figure 22:
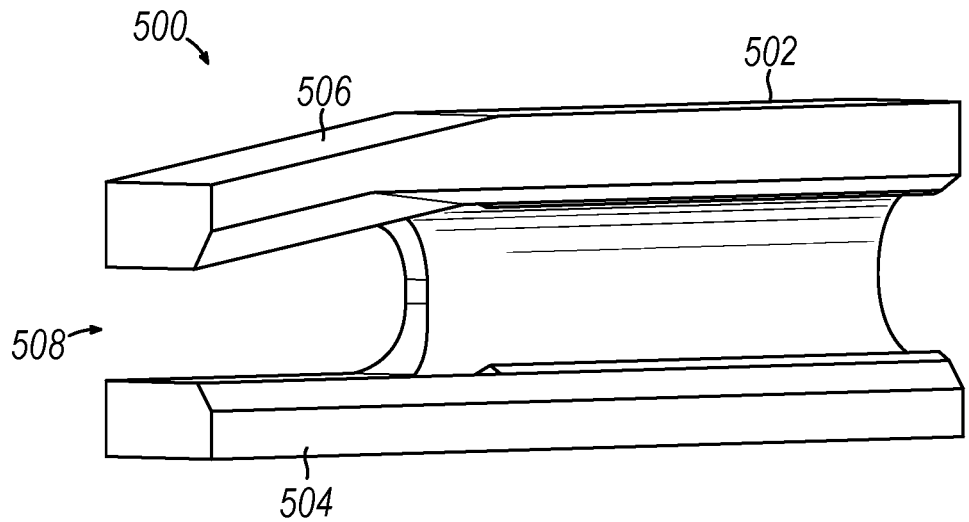
FIG. 22 depicts a perspective view of another exemplary end effector closure device configured for use with the surgical instrument of FIG. 1 and the adjunct applicator device of FIG. 11.

FIG. 22 shows another exemplary end effector closure device (500) that is operable to close end effector (12) onto an adjunct applicator device (not shown), such as adjunct applicator device (210), to apply one or more adjuncts to the stapling surfaces of end effector jaws (16, 18). Closure device (500) has a semi-cylindrical body (502), a lower elongate member (504) that extends distally from a lower distal end of body (502), and an upper elongate member (506) that extends distally from an upper distal end of body (502) and is angled downwardly toward lower elongate member (504). The free distal ends of lower and upper elongate members (504, 506) define a distal opening (508) that sized similar to a diameter of shaft (22) of stapler (10). In some versions, lower and upper elongate members (504, 506) may be rigid. In other version, upper member (506) may be formed with a predetermined degree of flexibility.

Figure 23A:
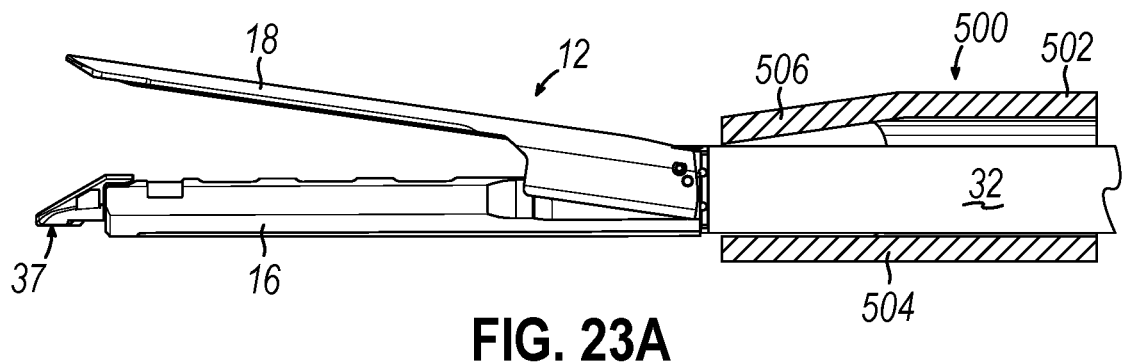
FIG. 23A depicts a partial cross-sectional side view of the end effector closure device of FIG. 22 applied to the surgical instrument of FIG. 1, showing the end effector closure device in a proximal position on the surgical instrument in which the end effector is permitted to assume an open state.
Figure 23B:
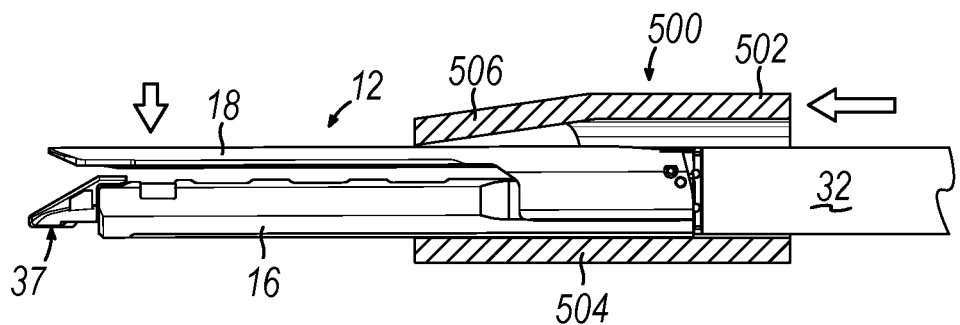
FIG. 23B depicts a partial cross-sectional side view of the end effector closure device and the surgical instrument of FIG. 23A, showing the end effector closure device having been translated to a distal position on the surgical instrument to force the end effector jaws shut onto an adjunct applicator device, which is omitted from view.

As shown in FIGS. 23A-23B, end effector closure device (500) is snapped onto stapler shaft (22) at a location proximal to end effector (12) and is slidable along shaft (22) like a sleeve. End effector (12) is then positioned about an adjunct applicator device (not shown), such as adjunct applicator device (210). Closure device (500) is then translated distally over shaft (22) so that lower and upper elongate members (504, 506) cooperate to force end effector jaws (16, 18) closed onto the adjunct applicator device, thereby applying one or more adjuncts to the stapling surfaces of jaws (16, 18). This distal translation of closure device (500) may also function to temporarily immobilize articulation joint (11) of stapler (10). Following application of the adjuncts to end effector jaws (16, 18), closure device (500) may be translated proximally to enable jaws (16, 18) to reopen and to free articulation joint (11).

D. End Effector Closure Device Having Sleeve with Pivotable Member

Figure 24A:
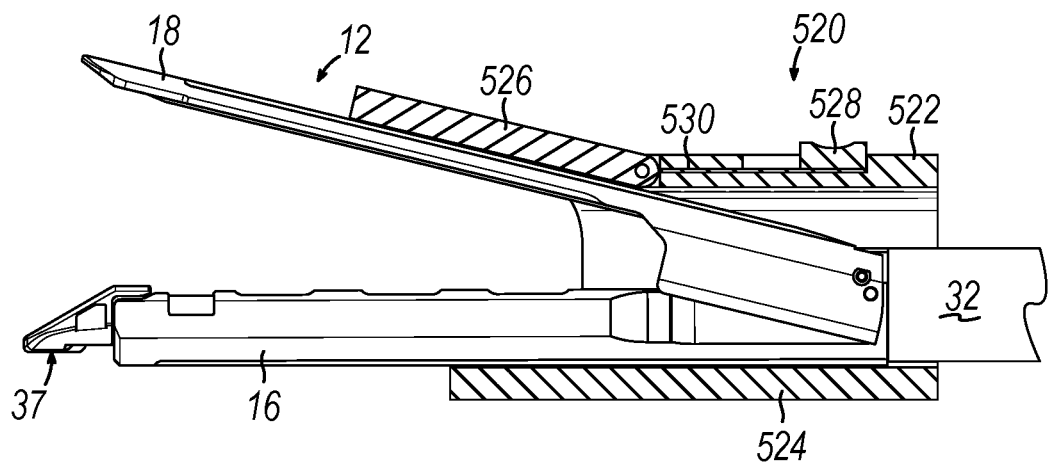
FIG. 24A depicts a partial cross-sectional side view of another exemplary end effector closure device applied to the surgical instrument of FIG. 1, showing an actuator of the end effector closure device in a proximal position and a closure member of the end effector closure device in a resulting open position such that the end effector is permitted to assume an open state.
Figure 24B:
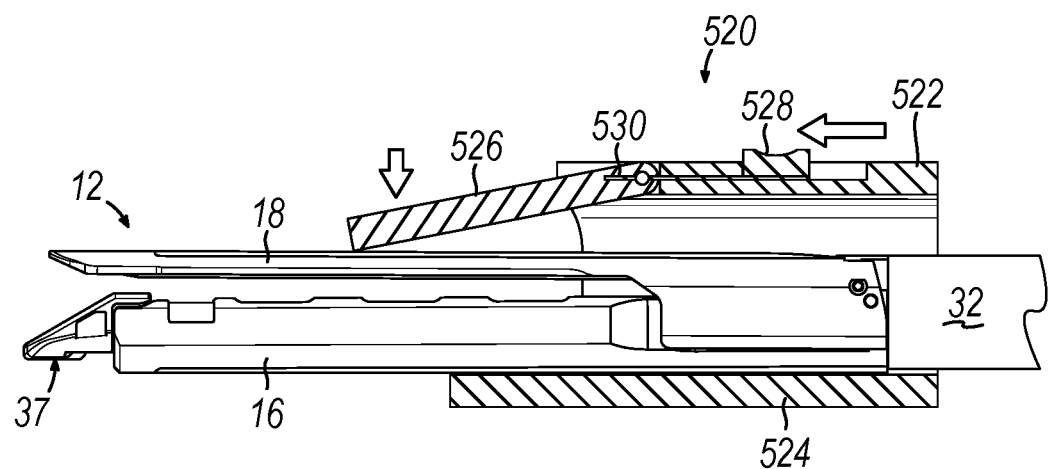
FIG. 24B depicts a partial cross-sectional side view of the end effector closure device and the surgical instrument of FIG. 24A, showing the actuator having been translated to a distal position to drive the closure member to a closed position to thereby close the end effector onto an adjunct applicator device, which is omitted from view.

FIGS. 24A-24B show another exemplary end effector closure device (520) that is operable to close end effector (12) onto an adjunct applicator device (not shown), such as adjunct applicator device (210), to apply one or more adjuncts to the stapling surfaces of end effector jaws (16, 18). Closure device (520) is similar to closure device (500) in that closure device (520) has a semi-cylindrical body (522), a lower elongate member (524) that extends distally from a lower distal end of body (522), and an upper elongate member (526) that extends distally from an upper distal end of body (522). Unlike closure device (500), upper elongate member (526) of closure device (520) is pivotably coupled with body (522) and is actuatable between a raised position shown in FIG. 24A and a lowered position shown in FIG. 24B by a translatable actuator (528). As shown in FIG. 24A, actuator (528) in a proximal position enables upper elongate member (526) to pivot upwardly relative to body (522) and thereby accommodate an open state of end effector (12). As shown in FIG. 24B, actuator (528) is driven distally by an operator so that a distal extension (530) of actuator (528) advances distally into an interior of upper elongate member (526), thus forcing upper elongate member (526) to pivot downwardly against anvil jaw (18) and forcing end effector (12) to close onto the adjunct applicator device to apply adjuncts to jaws (16, 18). Actuator (528) may then be returned to its proximal position to permit end effector (12) to reopen.

E. Closure Indicator Device

Figure 25:
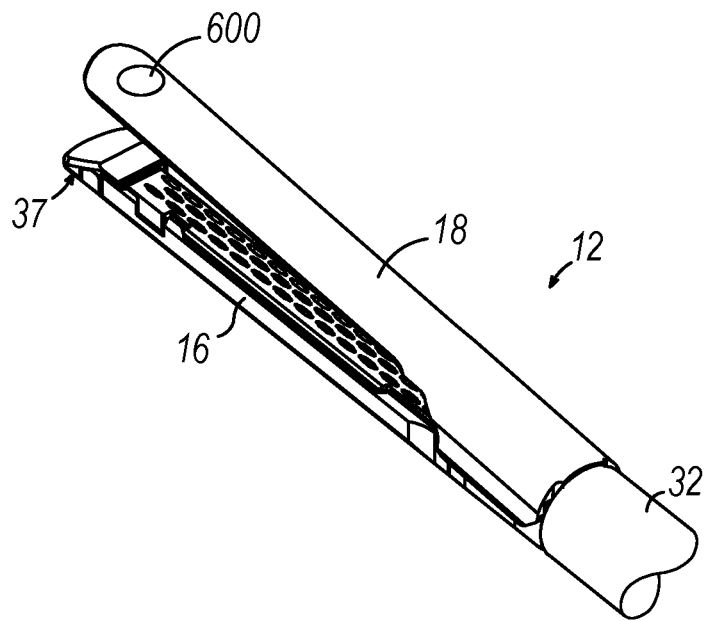
FIG. 25 depicts a perspective view of an exemplary closure indicator device applied to the anvil jaw of the end effector of FIG. 3, showing the end effector in an open state.
Figure 26:
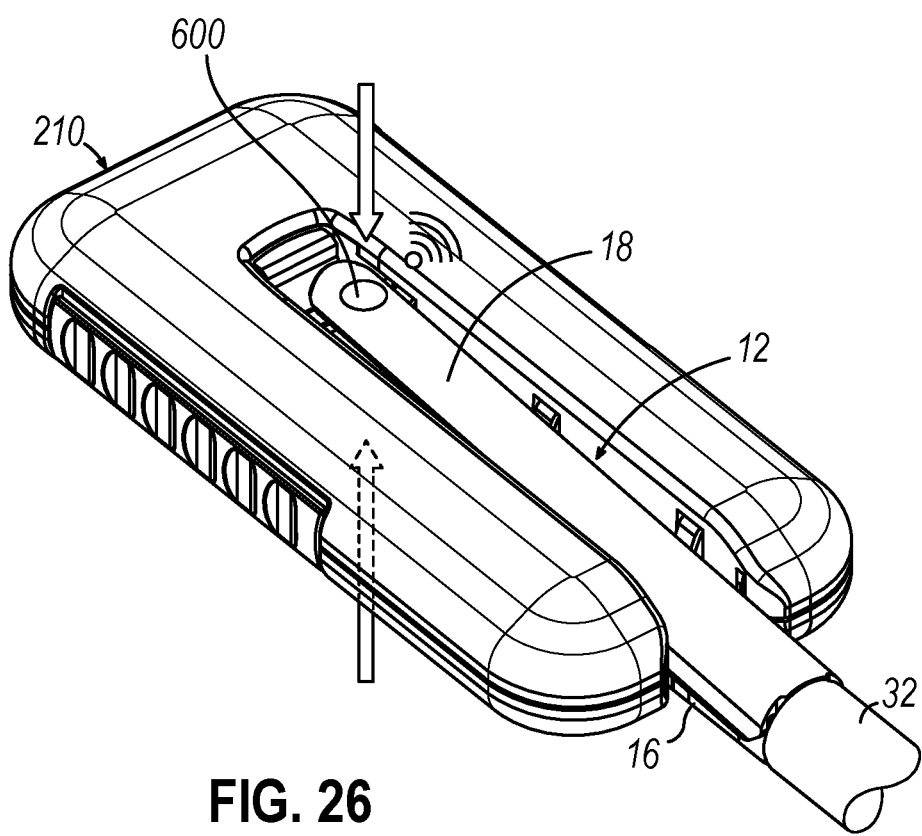
FIG. 26 depicts a perspective view of the end effector and closure indicator device of FIG. 25, showing the end effector having been closed onto the platform of the adjunct applicator device of FIG. 3 by hand by an operator so that the closure device indicator emits an indication to the operator.

In some instances, it may be desirable for an operator to close end effector (12) onto an adjunct applicator device, such as applicator device (210), by directly grasping end effector jaws (16, 18) with the operator's hand and without using an ancillary end effector closure device such as any of closure devices (300, 400, 500, 520) described above. FIGS. 25-26 show an exemplary closure indicator device (600) applied to an exterior surface of anvil jaw (18) of end effector (12) configured to assist an operator in such applications. Closure indicator device (600) is configured to emit feedback to the operator indicative of end effector (12) having been closed onto platform (218) of applicator device (210) to a predetermined closure state or with a predetermined threshold force sufficient to ensure application of buttress assemblies (110, 112) to end effector jaws (16, 18). Such feedback may be in any suitable form, such as tactile, audible, and/or visible feedback, for example. In an exemplary version, closure indicator device (600) may be in the form of a dome switch configured to toggle and thereby provide a tactile indication to the operator in response to the operator exerting a predetermined threshold force on closure indicator device (600) while closing end effector jaws (16, 18) onto applicator platform (218).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body having an interior space sized and shaped to receive a surgical stapler end effector in an open state in combination with an adjunct applicator that includes an adjunct; and (b) a closure member movably coupled with the body, wherein the closure member is actuatable to close the surgical stapler end effector onto the adjunct applicator so that the adjunct is applied to a stapling surface of the surgical stapler end effector.

Example 2

The apparatus of Example 1, wherein the body includes an open proximal end and a closed distal end, wherein the adjunct applicator is insertable distally through the open proximal end and into the interior space such that a distal end of the adjunct applicator faces the closed distal end of the body.

Example 3

The apparatus of any of Example 2, wherein the body further includes a bottom wall and a pair of side walls that extend longitudinally between the open proximal end and the closed distal end, wherein the closure member is movable within an opening defined between the side walls.

Example 4

The apparatus of any of the preceding Examples, wherein the body includes a bottom wall and an support structure extending upwardly from the bottom wall, wherein the support structure is configured to support an underside of the adjunct applicator.

Example 5

The apparatus of Example 4, wherein the support structure includes a pair of support members spaced apart from one another and configured to contact the underside of the adjunct applicator.

Example 6

The apparatus of Example 5, wherein the support members are resiliently biased in a direction away from the bottom wall, wherein the support members are configured to support and urge the adjunct applicator in a direction toward the closure member.

Example 7

The apparatus of any of Examples 5 through 6, wherein the support members comprise a pair of leaf springs.

Example 8

The apparatus of any of Examples 3 through 7, wherein the body further includes an end effector jaw support feature extending upwardly from the bottom wall, wherein the end effector jaw support feature is configured to contact a jaw of the surgical stapler end effector when the closure member is actuated to facilitate closure of the surgical stapler end effector onto the adjunct applicator.

Example 9

The apparatus of any of the preceding Examples, wherein the closure member is actuatable relative to the body from a first position to a second position to close the surgical stapler end effector onto the adjunct applicator, wherein the closure member is resiliently biased toward the first position.

Example 10

The apparatus of any of the preceding Examples, wherein the closure member comprises a lever pivotably coupled with the body, wherein the lever is pivotable toward the body to close the surgical stapler end effector onto the adjunct applicator, wherein the lever is pivotable away from the body to permit the end effector to resume an open state.

Example 11

The apparatus of Example 10, wherein a distal end of the lever is pivotably coupled with a distal end of the body.

Example 12

The apparatus of any of the preceding Examples, wherein the closure member includes a protrusion that extends toward the body and is configured to contact an exterior surface of a jaw of the surgical stapler end effector.

Example 13

The apparatus of Example 12, wherein the protrusion comprises a first protrusion, wherein the closure member further includes a second protrusion that is spaced apart from the first protrusion and extends toward the body, wherein the second protrusion is configured to promote alignment of the jaw with the apparatus and the adjunct applicator.

Example 14

A system comprising: (a) the apparatus of an of the preceding Examples; and (b) the adjunct applicator, wherein the adjunct applicator comprises: (i) an applicator body, (ii) a platform coupled with the applicator body, and (iii) the adjunct positioned on the platform, wherein the closure member of the apparatus is actuatable to close the surgical stapler end effector onto the platform so that the adjunct is applied to the stapling surface of the surgical stapler end effector.

Example 15

The system of Example 14, wherein the adjunct comprises a first adjunct positioned on a first side of the platform, wherein the adjunct applicator further includes a second adjunct positioned on a second side of the platform, wherein the closure member is actuatable to close the surgical stapler end effector onto the platform so that the first adjunct is applied to a first stapling surface of the surgical stapler end effector and the second adjunct is simultaneously applied to a second stapling surface of the surgical stapler end effector.

Example 16

A system comprising: (a) a first device, wherein the first device comprises: (i) a first device body, (ii) a platform coupled with the first device body, wherein the platform is configured to be positioned between a pair of stapling surfaces of a surgical stapler end effector in an open state, and (iii) an adjunct positioned on the platform; and (b) a second device, wherein the second device comprises: (i) a second device body configured to releasably receive and support the first device, and (ii) a closure member movably coupled with the second device body, wherein the closure member is actuatable to close the surgical stapler end effector onto the platform of the first device to apply the adjunct to one of the stapling surfaces of the surgical stapler end effector.

Example 17

The system of Example 16, wherein the second device body includes an open proximal end, wherein the first device is configured to be received through the open proximal end and into an interior space of the second device body.

Example 18

The system of any of Examples 16 through 17, wherein the closure member comprises a lever that is pivotably coupled with the second device body, wherein the lever is actuatable to directly contact and close the surgical stapler end effector on the platform of the first device.

Example 19

A method comprising: (a) coupling an adjunct applicator with an end effector closure device that is operable to close an end effector of a surgical stapler and is provided separately from the surgical stapler, wherein the adjunct applicator includes a platform and an adjunct positioned on the platform; (b) positioning the platform between first and second stapling surfaces of the end effector in an open state while the adjunct applicator remains coupled with the end effector closure device; and (c) actuating a movable closure member of the end effector closure device to contact an exterior of the end effector with the end effector closure device and thereby close the end effector onto the platform of the adjunct applicator.

Example 20

The method of Example 19, wherein coupling the adjunct applicator with the end effector closure device comprises inserting the adjunct applicator into an interior space of the end effector closure device.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
   (a) a body having an interior space sized and shaped to receive a surgical stapler end effector in an open state in combination with an adjunct applicator that includes an adjunct, wherein the body includes:
      (i) an open proximal end,
      (ii) a closed distal end, wherein the adjunct applicator is insertable distally through the open proximal end and into the interior space such that a distal end of the adjunct applicator faces the closed distal end,
      (iii) a bottom wall, and
      (iv) a pair of side walls that extend longitudinally between the open proximal end and the closed distal end; and
   (b) a closure driver movably coupled with the body, wherein the closure driver is actuatable to close the surgical stapler end effector onto the adjunct applicator so that the adjunct is applied to a stapling surface of the surgical stapler end effector, wherein the closure driver is movable between the side walls.

2. The apparatus of claim 1, wherein the body includes a support structure extending upwardly from the bottom wall, wherein the support structure is configured to support an underside of the adjunct applicator.

3. The apparatus of claim 2, wherein the support structure includes a pair of support members spaced apart from one another and configured to contact the underside of the adjunct applicator.

4. The apparatus of claim 3, wherein the support members are resiliently biased in a direction away from the bottom wall, wherein the support members are configured to support and urge the adjunct applicator in a direction toward the closure driver.

5. The apparatus of claim 4, wherein the support members comprise a pair of leaf springs.

6. The apparatus of claim 2, wherein the body further includes an end effector jaw support feature extending upwardly from the bottom wall, wherein the end effector jaw support feature is configured to contact a jaw of the surgical stapler end effector when the closure driver is actuated to facilitate closure of the surgical stapler end effector onto the adjunct applicator.

7. The apparatus of claim 1, wherein the closure driver is actuatable relative to the body from a first position to a second position to close the surgical stapler end effector onto the adjunct applicator, wherein the closure driver is resiliently biased toward the first position.

8. The apparatus of claim 1, wherein the closure driver comprises a lever pivotably coupled with the body, wherein the lever is pivotable toward the body to close the surgical stapler end effector onto the adjunct applicator, wherein the lever is pivotable away from the body to permit the end effector to resume an open state.

9. The apparatus of claim 8, wherein a distal end of the lever is pivotably coupled with a distal end of the body.

10. The apparatus of claim 1, wherein the closure driver includes a protrusion that extends toward the body and is configured to contact an exterior surface of a jaw of the surgical stapler end effector.

11. The apparatus of claim 10, wherein the protrusion comprises a first protrusion, wherein the closure driver further includes a second protrusion that is spaced apart from the first protrusion and extends toward the body, wherein the second protrusion is configured to promote alignment of the jaw with the apparatus and the adjunct applicator.

12. A system comprising:
   (a) the apparatus of claim 1; and
   (b) the adjunct applicator, wherein the adjunct applicator comprises:
      (i) an applicator body,
      (ii) a platform coupled with the applicator body, and
      (iii) the adjunct positioned on the platform,
   wherein the closure driver of the apparatus is actuatable to close the surgical stapler end effector onto the platform so that the adjunct is applied to the stapling surface of the surgical stapler end effector.

13. The system of claim 12, wherein the adjunct comprises a first adjunct positioned on a first side of the platform, wherein the adjunct applicator further includes a second adjunct positioned on a second side of the platform, wherein the closure driver is actuatable to close the surgical stapler end effector onto the platform so that the first adjunct is applied to a first stapling surface of the surgical stapler end effector and the second adjunct is simultaneously applied to a second stapling surface of the surgical stapler end effector.

14. A system comprising:
   (a) a first device, wherein the first device comprises:
      (i) a first device body,
      (ii) a platform coupled with the first device body, wherein the platform is configured to be positioned between a pair of stapling surfaces of a surgical stapler end effector in an open state, and
      (iii) an adjunct positioned on the platform; and
   (b) a second device, wherein the second device comprises:
      (i) a second device body configured to releasably receive and support the first device, wherein the first device is selectively insertable into and removable from the second device body, and
      (ii) a closure driver movably coupled with the second device body, wherein the closure driver is actuatable to close the surgical stapler end effector onto the platform of the first device to apply the adjunct to one of the stapling surfaces of the surgical stapler end effector.

15. The system of claim 14, wherein the second device body includes an open proximal end, wherein the first device is configured to be received through the open proximal end and into an interior space of the second device body.

16. The system of claim 14, wherein the closure driver comprises a lever that is pivotably coupled with the second device body, wherein the lever is actuatable to directly contact and close the surgical stapler end effector on the platform of the first device.

17. A method comprising:
   (a) removably coupling an adjunct applicator with an end effector closure device such that the adjunct applicator is selectively removable from the end effector closure device, wherein the end effector closure device is operable to close an end effector of a surgical stapler and is provided separately from the surgical stapler, wherein the adjunct applicator includes a platform and an adjunct positioned on the platform;
   (b) positioning the platform between first and second stapling surfaces of the end effector in an open state while the adjunct applicator remains coupled with the end effector closure device; and
   (c) actuating a movable closure driver of the end effector closure device to contact an exterior of the end effector with the end effector closure device and thereby close the end effector onto the platform of the adjunct applicator.

18. The method of claim 17, wherein removably coupling the adjunct applicator with the end effector closure device comprises distally inserting the adjunct applicator into an interior space of the end effector closure device.

19. The apparatus of claim 14, wherein the first device body defines an open proximal end and a closed distal end of the first device, wherein the platform is proximally exposed at the open proximal end.

20. The apparatus of claim 17, wherein the adjunct applicator is movable vertically within the end effector closure device when the closure driver is actuated to close the end effector onto the platform.

* * * * *